United States Patent
Tian et al.

(10) Patent No.: US 10,800,821 B2
(45) Date of Patent: Oct. 13, 2020

(54) RECOMBINANT BI-FUNCTIONAL FUSION PROTEIN AND PREPARATION AND APPLICATION THEREFOR

(71) Applicant: IMMUNEONCO BIOPHARMACEUTICALS (SHANGHAI) CO., LTD, Shanghai (CN)

(72) Inventors: Wenzhi Tian, Shanghai (CN); Deqiang Jing, Shanghai (CN)

(73) Assignee: IMMUNEONCO BIOPHARMACEUTICALS (SHANGHAI) CO., LTD, Shanghai (CN)

( * ) Notice: Subject to any disclaimer, the term of this patent is extended or adjusted under 35 U.S.C. 154(b) by 150 days.

(21) Appl. No.: 15/566,724

(22) PCT Filed: Nov. 16, 2015

(86) PCT No.: PCT/CN2015/094739
§ 371 (c)(1),
(2) Date: Oct. 16, 2017

(87) PCT Pub. No.: WO2016/169261
PCT Pub. Date: Oct. 27, 2016

(65) Prior Publication Data
US 2018/0141986 A1    May 24, 2018

(30) Foreign Application Priority Data

Apr. 24, 2015   (CN) .......................... 2015 1 0203619

(51) Int. Cl.
| | | |
|---|---|---|
| *C07K 14/705* | (2006.01) | |
| *C07K 19/00* | (2006.01) | |
| *C07K 14/47* | (2006.01) | |
| *C12N 5/10* | (2006.01) | |
| *A61K 39/395* | (2006.01) | |
| *C12N 15/63* | (2006.01) | |
| *C12N 15/62* | (2006.01) | |
| *A61P 11/06* | (2006.01) | |
| *A61P 19/02* | (2006.01) | |
| *A61P 35/02* | (2006.01) | |
| *A61P 1/00* | (2006.01) | |
| *A61P 35/00* | (2006.01) | |
| *A61K 38/00* | (2006.01) | |

(52) U.S. Cl.
CPC ........ *C07K 14/4702* (2013.01); *A61K 39/395* (2013.01); *A61P 1/00* (2018.01); *A61P 11/06* (2018.01); *A61P 19/02* (2018.01); *A61P 35/00* (2018.01); *A61P 35/02* (2018.01); *C07K 19/00* (2013.01); *C12N 5/10* (2013.01); *C12N 15/62* (2013.01); *C12N 15/63* (2013.01); *A61K 38/00* (2013.01); *C07K 2319/30* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 2003/0026803 A1* | 2/2003 | Barclay | C07K 16/2803 424/144.1 |
| 2009/0186025 A1* | 7/2009 | Colaco | C07K 14/005 424/134.1 |

OTHER PUBLICATIONS

Burgess et al., J of Cell Bio. 111:2129-2138, 1990 (Year: 1990).*
Lazar et al. Molecular and Cellular Biology 8:1247-1252, 1988 (Year: 1988).*
Ju (Proceedings of the National Academy of Sciences, U.S.A., vol. 88, p. 2658-2662, 1991) (Year: 1991).*
Baker (Immunity, vol. 13, p. 475-484, 2000) (Year: 2000).*
Bowie et al. Science, 247:1306-1310, 1990, p. 1306, col. 2 (Year: 1990).*
Martindale (Nature Genetics, vol. 18, p. 150-154, 1998) (Year: 1998).*
Nonaka (Human Molecular Genetics, vol. 18, No. 18, p. 3353-3364, 2009) (Year: 2009).*
Gardai SJ et al.,Cell-surface calreticulin initiates clearance of viable or apoptotic cells through trans-activation of LRP on the phagocyte. Cell.2005;123:321-334.
Obeid M et al., Calreticulin exposure is required for the immunogenicity of gamma-irradiation and UVC lightinduced apoptosis.Cell Death Differ.2007;14:1848-1850.
Orr Aw et al., Low density lipoprotein receptor-related protein is a calreticulin coreceptor that signals focal adhesion disassembly.J Cell Biol.2003;161:1179-1189.
Theocharides A.P.A et al., Disruption of SIRPalpha signaling in macrophages eliminates human acute myeloid leukemia stem cells in xenografts. J Exp Med.2012;209(10):1883-1899.
Lee WY et al., Novel structural determinants on SIRP alpha that mediate binding to CD47 . . . J Immunol. 2007;179(11):7741-7750.

(Continued)

*Primary Examiner* — Michael Allen
(74) *Attorney, Agent, or Firm* — Duane Morris LLP; Thomas J. Kowalski; Deborah L. Lu

(57) ABSTRACT

The present invention provides a recombinant fusion protein containing a first extracellular Ig-like domain of a signal-regulator protein alpha (SIRPα), linked to an Fc fragment of a human IgG1. The present invention also provides a polynucleotide encoding the recombinant fusion protein, an expression vector containing the polynucleotide, a method for producing the recombinant protein and a method for treating a disease caused by over expression of CD47.

13 Claims, 8 Drawing Sheets
Specification includes a Sequence Listing.

(56) References Cited

OTHER PUBLICATIONS

Tseng D et al., Anti-CD47 antibody-mediated phagocytosis of cancer by macrophages primes an effective antitumor T-cell respose. PNAS.2013;110:11103-11108.

Van Der Poll T et al, Effect of a Recombinant Dimeric Tumor Necrosis Factor Receptor on Inflammatory Responses to Intravenous Endotoxin in Normal Humans, Blood,May 15, 1997; 89(10): 3727-34.

Shields RL et al., High Resolution Mapping of the Binding Site on Human IgG1 for FcγRI, FcγRII, FcγRIII, and FcRn and Design of IgG1 Variants with Improved Binding to the FcγR The Journal of Biological Chemistry (2001), vol. 276, No. 9, Issue of Mar. 2, pp. 6591-6604, printed in US.

John Richards et al, Optimization of antibody binding to FcgammaRIIa enhances macrophage phagocytosis of tumor cells, Mol. Cancer Ther 2008; 7(8). Aug. 2008; 2517-2527.

G.A. Lazer et al, Engineered antibody Fc variants with enhanced effector function, Proc. Natl. Acad. Sci. USA 103 (2006) 4005-4010.

* cited by examiner

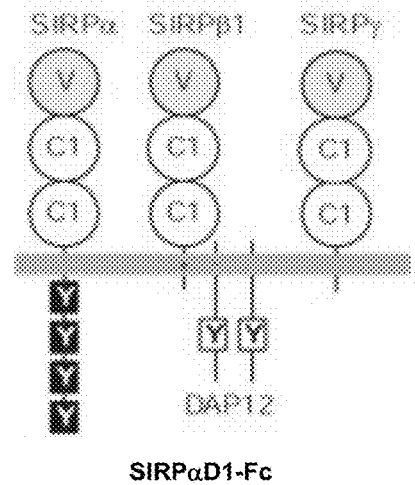
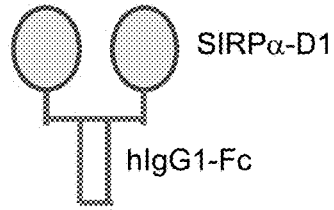
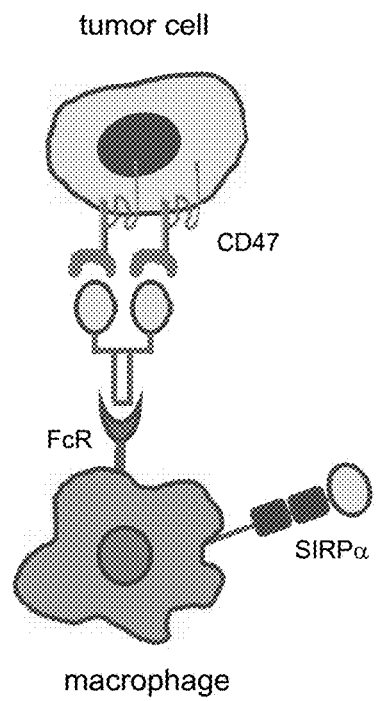
FIG. 1A    FIG. 1B    FIG. 1C
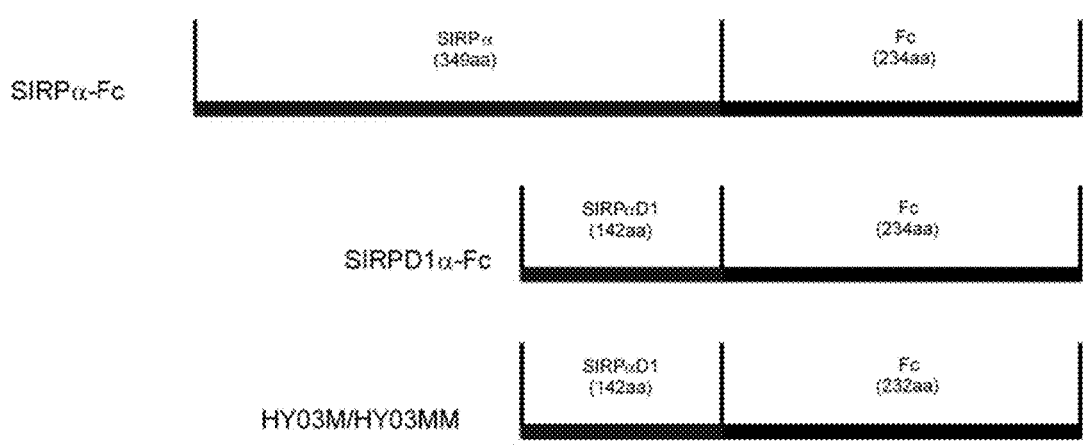
FIG. 1D

TCCTGCGCCT GGTCAGGAGT GGCGGGTGAG GAGGAGCTGC AGGTGATTCA GCCTGACAAG 60
TCCGTATCAG TTGCAGCTGG AGAGTCGGCC ATTCTGCACT GCACTGTGAC CTCCCTGATC 120
CCTGTGGGGC CCATCCAGTG GTTCAGAGGA GCTGGACCAG CCCGGGAATT AATCTACAAT 180
CAAAAAGAAG GCCACTTCCC CCGGGTAACA ACTGTTTCAG AGTCCACAAA GAGAGAAAAC 240
ATGGACTTTT CCATCAGCAT CAGTAACATC ACCCCAGCAG ATGCCGGCAC CTACTACTGT 300
GTGAAGTTCC GGAAAGGGAG CCCTGACACG GAGTTTAAGT CTGGAGCAGG CACTGAGCTG 360
TCTGTGCGTG CCAAACCCTC TGCCCCCGTG GTATCGGGCC CTGCGGCGAG GGCCACACCT 420
CAGCACACAG TGAGCTTCAC CTGCGAGTCC CACGGCTTCT CACCCAGAGA CATCACCCTG 480
AAATGGTTCA AAAATGGGAA TGAGCTCTCA GACTTCCAGA CCAACGTGGA CCCCGTAGGA 540
GAGAGCGTGT CCTACAGCAT CCACAGCACA GCCAAGGTGG TGCTGACCCG CGAGGACGTT 600
CACTCTCAAG TCATCTGCGA GGTGGCCCAC GTCACCTTGC AGGGGGACCC TCTTCGTGGG 660
ACTGCCAACT TGTCTGAGAC CATCCGAGTT CCACCCACCT TGGAGGTTAC TCAACAGCCC 720
GTGAGGGCAG AGAACCAGGT GAATGTCACC TGCCAGGTGA GGAAGTTCTA CCCCCAGAGA 780
CTACAGCTGA CCTGGTTGGA GAATGGAAAC GTGTCCCGGA CAGAAACGGC CTCAACCGTT 840
ACAGAGAACA AGGATGGTAC CTACAACTGG ATGAGCTGGC TCCTGGTGAA TGTATCTGCC 900
CACAGGGATG ATGTGAAGCT CACCTGCCAG GTGGAGCATG ACGGGCAGCC AGCGGTCAGC 960
AAAAGCCATG ACCTGAAGGT CTCAGCCCAC CCGAAGGAGC AGGGCTCAAA TACCGCCGCT 1020
GAGAACACTG GATCTAATGA ACGGAACGAA TTC*GAGCCCA AATCTTGTGA CAAAACTCAC* 1080
*ACATGCCCAC CGTGCCCAGC ACCTGAACTC CTGGGGGGAC CGTCAGTCTT CCTCTTCCCC* 1140
*CCAAAACCCA AGGACACCCT CATGATCTCC CGGACCCCTG AGGTCACATG CGTGGTGGTG* 1200
*GACGTGAGCC ACGAAGACCC TGAGGTCAAG TTCAACTGGT ACGTGGACGG CGTGGAGGTG* 1260
*CATAATGCCA AGACAAAGCC GCGGGAGGAG CAGTACAACA GCACGTACCG TGTGGTCAGC* 1320
*GTCCTCACCG TCCTGCACCA GGACTGGCTG AATGGCAAGG AGTACAAGTG CAAGGTCTCC* 1380
*AACAAAGCCC TCCCAGCCCC CATCGAGAAA ACCATCTCCA AAGCCAAAGG GCAGCCCCGA* 1440
*GAACCACAGG TGTACACCCT GCCCCCATCC CGGGATGAGC TGACCAAGAA CCAGGTCAGC* 1500
*CTGACCTGCC TGGTCAAAGG CTTCTATCCC AGCGACATCG CCGTGGAGTG GGAGAGCAAT* 1560
*GGGCAGCCGG AGAACAACTA CAAGACCACG CCTCCCGTGC TGGACTCCGA CGGCTCCTTC* 1620
*TTCCTCTACA GCAAGCTCAC CGTGGACAAG AGCAGGTGGC AGCAGGGGAA CGTCTTCTCA* 1680
*TGCTCCGTGA TGCATGAGGC TCTGCACAAC CACTACACGC AGAAGAGCCT CTCCCTGTCT* 1740
*CCGGGTAAAT GA* (SEQ ID NO.:1)

FIG. 2A

SCAWSGVAGEEELQVIQPDKSVSVAAGESAILHCTVTSLIPVGPIQWFRGAGPARELIYN 60
QKEGHFPRVTTVSESTKRENMDFSISISNITPADAGTYYCVKFRKGSPDTEFKSGAGTEL 120
SVRAKPSAPVVSGPAARATPQHTVSFTCESHGFSPRDITLKWFKNGNELSDFQTNVDPVG 180
ESVSYSIHSTAKVVLTREDVHSQVICEVAHVTLQGDPLRGTANLSETIRVPPTLEVTQQP 240
VRAENQVNVTCQVRKFYPQRLQLTWLENGNVSRTETASTVTENKDGTYNWMSWLLVNVSA 300
HRDDVKLTCQVEHDGQPAVSKSHDLKVSAHPKEQGSNTAAENTGSNERNEFEPKSCDKTH 360
TCPPCPAPELLGGPSVFLFPPKPKDTLMISRTPEVTCVVVDVSHEDPEVKFNWYVDGVEV 420
HNAKTKPREEQYNSTYRVVSVLTVLHQDWLNGKEYKCKVSNKALPAPIEKTISKAKGQPR 480
EPQVYTLPPSRDELTKNQVSLTCLVKGFYPSDIAVEWESNGQPENNYKTTPPVLDSDGSF 540
FLYSKLTVDKSRWQQGNVFSCSVMHEALHNHYTQKSLSLSPGK 583 (SEQ ID NO.:2)

FIG. 2B

TCCTGCGCCT GGTCAGGAGT GGCGGGTGAG GAGGAGCTGC AGGTGATTCA GCCTGACAAG 60
TCCGTATCAG TTGCAGCTGG AGAGTCGGCC ATTCTGCACT GCACTGTGAC CTCCCTGATC 120
CCTGTGGGGC CCATCCAGTG GTTCAGAGGA GCTGGACCAG CCCGGGAATT AATCTACAAT 180
CAAAAAGAAG GCCACTTCCC CCGGGTAACA ACTGTTTCAG AGTCCACAAA GAGAGAAAAC 240
ATGGACTTTT CCATCAGCAT CAGTAACATC ACCCCAGCAG ATGCCGGCAC CTACTACTGT 300
GTGAAGTTCC GGAAAGGGAG CCCTGACACG GAGTTTAAGT CTGGAGCAGG CACTGAGCTG 360
TCTGTGCGTG CCAAACCCTC TGCCCCCGTG GTATCGGGCC CTGCGGCGAG GGCCACACCT 420
CAGCAC*GAAT TCGAGCCCAA ATCTTGTGAC AAAACTCACA CATGCCCACC GTGCCCAGCA* 480
*CCTGAACTCC TGGGGGGACC GTCAGTCTTC CTCTTCCCCC CAAAACCCAA GGACACCCTC* 540
*ATGATCTCCC GGACCCCTGA GGTCACATGC GTGGTGGTGG ACGTGAGCCA CGAAGACCCT* 600
*GAGGTCAAGT TCAACTGGTA CGTGGACGGC GTGGAGGTGC ATAATGCCAA GACAAAGCCG* 660
*CGGGAGGAGC AGTACAACAG CACGTACCGT GTGGTCAGCG TCCTCACCGT CCTGCACCAG* 720
*GACTGGCTGA ATGGCAAGGA GTACAAGTGC AAGGTCTCCA ACAAAGCCCT CCCAGCCCCC* 780
*ATCGAGAAAA CCATCTCCAA AGCCAAAGGG CAGCCCCGAG AACCACAGGT GTACACCCTG* 840
*CCCCCATCCC GGGATGAGCT GACCAAGAAC CAGGTCAGCC TGACCTGCCT GGTCAAAGGC* 900
*TTCTATCCCA GCGACATCGC CGTGGAGTGG GAGAGCAATG GGCAGCCGGA GAACAACTAC* 960
*AAGACCACGC CTCCCGTGCT GGACTCCGAC GGCTCCTTCT TCCTCTACAG CAAGCTCACC* 1020
*GTGGACAAGA GCAGGTGGCA GCAGGGGAAC GTCTTCTCAT GCTCCGTGAT GCATGAGGCT* 1080
*CTGCACAACC ACTACACGCA GAAGAGCCTC TCCCTGTCTC CGGGTAAATA G* (SEQ ID NO.:3)

FIG. 3A

SCAWSGVAGEEELQVIQPDKSVSVAAGESAILHCTVTSLIPVGPIQWFRGAGPARELIYN 60
QKEGHFPRVTTVSESTKRENMDFSISISNITPADAGTYYCVKFRKGSPDTEFKSGAGTEL 120
SVRAKPSAPVVSGPAARATPQHEF*EPKSCDKTHTCPPCPAPELLGGPSVFLFPPKPKDTL* 180
*MISRTPEVTCVVVDVSHEDPEVKFNWYVDGVEVHNAKTKPREEQYNSTYRVVSVLTVLHQ* 240
*DWLNGKEYKCKVSNKALPAPIEKTISKAKGQPREPQVYTLPPSRDELTKNQVSLTCLVKG* 300
*FYPSDIAVEWESNGQPENNYKTTPPVLDSDGSFFLYSKLTVDKSRWQQGNVFSCSVMHEA* 360
*LHNHYTQKSLSLSPGK* 376 (SEQ ID NO.:4)

FIG. 3B

```
TCCTGCGCCT GGTCAGGAGT GGCGGGTGAG GAGGAGCTGC AGGTGATTCA GCCTGACAAG 60
TCCGTATCAG TTGCAGCTGG AGAGTCGGCC ATTCTGCACT GCACTGTGAC CTCCCTGATC 120
CCTGTGGGGC CCATCCAGTG GTTCAGAGGA GCTGGACCAG CCCGGGAATT AATCTACAAT 180
CAAAAAGAAG GCCACTTCCC CCGGGTAACA ACTGTTTCAG AGTCCACAAA GAGAGAAAAC 240
ATGGACTTTT CCATCAGCAT CAGTGCCATC ACCCCAGCAG ATGCCGGCAC CTACTACTGT 300
GTGAAGTTCC GGAAAGGGAG CCCTGACACG GAGTTTAAGT CTGGAGCAGG CACTGAGCTG 360
TCTGTGCGTG CCAAACCCTC TGCCCCGTG GTATCGGGCC CTGCGGCGAG GGCCACACCT 420
CAGCACGAGC CCAAATCTTG TGACAAAACT CACACATGCC CACCGTGCCC AGCACCTGAA 480
CTCCTGGGGG GACCGTCAGT CTTCCTCTTC CCCCCAAAAC CCAAGGACAC CCTCATGATC 540
TCCCGGACCC CTGAGGTCAC ATGCGTGGTG GTGGACGTGA GCCACGAAGA CCCTGAGGTC 600
AAGTTCAACT GGTACGTGGA CGGCGTGGAG GTGCATAATG CCAAGACAAA GCCGCGGGAG 660
GAGCAGTACA ACAGCACGTA CCGTGTGGTC AGCGTCCTCA CCGTCCTGCA CCAGGACTGG 720
CTGAATGGCA AGGAGTACAA GTGCAAGGTC TCCAACAAAG CCCTCCCAGC CCCCATCGAG 780
AAAACCATCT CCAAAGCCAA AGGGCAGCCC CGAGAACCAC AGGTGTACAC CCTGCCCCCA 840
TCCCGGGATG AGCTGACCAA GAACCAGGTC AGCCTGACCT GCCTGGTCAA AGGCTTCTAT 900
CCCAGCGACA TCGCCGTGGA GTGGGAGAGC AATGGGCAGC CGGAGAACAA CTACAAGACC 960
ACGCCTCCCG TGCTGGACTC CGACGGCTCC TTCTTCCTCT ACAGCAAGCT CACCGTGGAC 1020
AAGAGCAGGT GGCAGCAGGG GAACGTCTTC TCATGCTCCG TGATGCATGA GGCTCTGCAC 1080
AACCACTACA CGCAGAAGAG CCTCTCCCTG TCTCCGGGTA AATAG (SEQ ID NO.:5)
```

FIG. 4A

```
SCAWSGVAGEEELQVIQPDKSVSVAAGESAILHCTVTSLIPVGPIQWFRGAGPARELIYN  60
QKEGHFPRVTTVSESTKRENMDFSISISAITPADAGTYYCVKFRKGSPDTEFKSGAGTEL  120
SVRAKPSAPVVSGPAARATPQHEPKSCDKTHTCPPCPAPELLGGPSVFLFPPKPKDTLMI  180
SRTPEVTCVVVDVSHEDPEVKFNWYVDGVEVHNAKTKPREEQYNSTYRVVSVLTVLHQDW  240
LNGKEYKCKVSNKALPAPIEKTISKAKGQPREPQVYTLPPSRDELTKNQVSLTCLVKGFY  300
PSDIAVEWESNGQPENNYKTTPPVLDSDGSFFLYSKLTVDKSRWQQGNVFSCSVMHEALH  360
NHYTQKSLSLSPGK  374 (SEQ ID NO.:6)
```

FIG. 4B

```
TCCTGCGCCT GGTCAGGAGT GGCGGGTGAG GAGGAGCTGC AGGTGATTCA GCCTGACAAG  60
TCCGTATCAG TTGCAGCTGG AGAGTCGGCC ATTCTGCACT GCACTGTGAC CTCCCTGATC 120
CCTGTGGGGC CCATCCAGTG GTTCAGAGGA GCTGGACCAG CCCGGGAATT AATCTACAAT 180
CAAAAAGAAG GCCACTTCCC CCGGGTAACA ACTGTTTCAG AGTCCACAAA GAGAGAAAAC 240
ATGGACTTTT CCATCAGCAT CAGTGCCATC ACCCCAGCAG ATGCCGGCAC CTACTACTGT 300
GTGAAGTTCC GGAAAGGGAG CCCTGACACG GAGTTTAAGT CTGGAGCAGG CACTGAGCTG 360
TCTGTGCGTG CCAAACCCTC TGCCCCCGTG GTATCGGGCC CTGCGGCGAG GGCCACACCT 420
CAGCAC GAGC CCAAATCTTG TGACAAAACT CACACATGCC CACCGTGCCC AGCACCTGAA 480
CTCCTGGGGG GACCGTCAGT CTTCCTCTTC CCCCCAAAAC CCAAGGACAC CCTCATGATC 540
TCCCGGACCC CTGAGGTCAC ATGCGTGGTG GTGGCCGTGA GCCACGAAGA CCCTGAGGTC 600
AAGTTCAACT GGTACGTGGA CGGCGTGGAG GTGCATAATG CCAAGACAAA GCCGCGGGAG 660
GAGCAGTACA ACAGCACGTA CCGTGTGGTC AGCGTCCTCA CCGTCCTGCA CCAGGACTGG 720
CTGAATGGCA AGGAGTACAA GTGCAAGGTC TCCAACAAAG CCCTCCCAGC CCCCATCGAG 780
AAAACCATCT CCAAAGCCAA AGGGCAGCCC CGAGAACCAC AGGTGTACAC CCTGCCCCCA 840
TCCCGGGATG AGCTGACCAA GAACCAGGTC AGCCTGACCT GCCTGGTCAA AGGCTTCTAT 900
CCCAGCGACA TCGCCGTGGA GTGGGAGAGC AATGGGCAGC CGGAGAACAA CTACAAGACC 960
ACGCCTCCCG TGCTGGACTC CGACGGCTCC TTCTTCCTCT ACAGCAAGCT CACCGTGGAC 1020
AAGAGCAGGT GGCAGCAGGG GAACGTCTTC TCATGCTCCG TGATGCATGA GGCTCTGCAC 1080
AACCACTACA CGCAGAAGAG CCTCTCCCTG TCTCCGGGTA AATAG (SEQ ID NO.:7)
```

FIG. 5A

```
SCAWSGVAGEEELQVIQPDKSVSVAAGESAILHCTVTSLIPVGPIQWFRGAGPARELIYN  60
QKEGHFPRVTTVSESTKRENMDFSISISAITPADAGTYYCVKFRKGSPDTEFKSGAGTEL 120
SVRAKPSAPVVSGPAARATPQH EPKSCDKTHTCPPCPAPELLGGPSVFLFPPKPKDTLMI 180
SRTPEVTCVVVAVSHEDPEVKFNWYVDGVEVHNAKTKPREEQYNSTYRVVSVLTVLHQDW 240
LNGKEYKCKVSNKALPAPIEKTISKAKGQPREPQVYTLPPSRDELTKNQVSLTCLVKGFY 300
PSDIAVEWESNGQPENNYKTTPPVLDSDGSFFLYSKLTVDKSRWQQGNVFSCSVMHEALH 360
NHYTQKSLSLSPGK 374 (SEQ ID NO.:8)
```

FIG. 5B

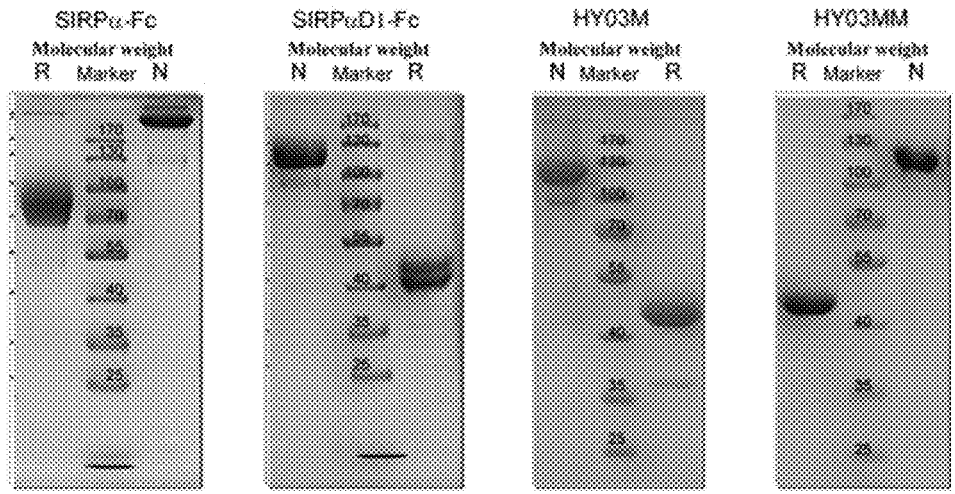

FIG. 6A  FIG. 6B  FIG. 6C  FIG. 6D

RECOMBINANT BI-FUNCTIONAL FUSION PROTEIN AND PREPARATION AND APPLICATION THEREFOR

FIELD OF THE INVENTION

The invention relates to a recombinant bi-functional fusion protein, preparation and use thereof, especially its use in tumor therapies.

BACKGROUND OF THE INVENTION

Cancer cells have developed some mechanisms to evade a host's immune surveillance so that they can grow faster. Among the mechanisms, the following three are well known. 1) To evade immune surveillance by T-lymphocytes. The cancer cells usually express a high level of membrane protein PD-L1 and PD-L2, both of which bind to PD-1 on the surface of T-cell, inducing T-cell apoptosis. 2) To evade immune surveillance by natural killer (NK) cells. The NKG2D protein on the surface of NK cells, upon binding to the MICA/MICB proteins on the surface of the cancer cells, can activate NK cells to kill the cancer cells. However, cancer cells have developed a mechanism that promotes the detachment of MICA/MICB from the cell membranes. The detached MICA/MICB binds to the NKG2D on the surface of NK cells, blocking the binding of NKG2D to MICA/MICB on the surface of cancer cells. 3) To evade the immune surveillance by macrophages (Mφ). Almost all cancer cells express on their surfaces a high level of CD47, which binds to the signal regulatory protein (SIRPα) on the surface of Mφ, thereby inducing the production of an inhibitory signal, which inhibits the phagocytosis of cancer cells by Mφ. It can be seen that the cancer cells are quite "smart" and reproduce quickly depending on their developed evasion mechanisms. Accordingly, development of effective anti-cancer drugs for killing all the cancer cells needs to target these mechanisms.

The present invention is directed to the signal regulatory protein SIRPα. The signal regulatory protein (SIRP) is a transmembrane glycoprotein, including three family members, SIRPα (CD172a), SIRPβ (CD172b) and SIRPγ (CD172g). The three proteins have similar extracellular regions but distinct cytoplasmic regions (FIG. 1A). The extracellular region contains three immunoglobulin (Ig) domains—one IgV-set and two IgC-set domains. The cytoplasmic region of SIRPα (CD172a) contains two domains which transmit inhibitory signals to inhibit the corresponding function(s) of the cell. SIRPβ (CD172b) and SIRPγ (CD172g) have very short cytoplasmic regions without any signal-transmitting domain. However, SIRPβ (CD172b) may transmit the activating signals through its association with the adaptor proteins such as DAP12 (FIG. 1). SIRPs are mainly expressed in macrophages (Mφ), dendritic cells (DCs) and neurons.

CD47 is also a transmembrane glycoprotein belonging to the immunoglobulin superfamily, and is expressed on the surface of all cell types including red blood cells. Ligands for CD47 include integrins, thrombospondin-1 and SIRPs. CD47 has many biological functions, including in cell migration, activation of T-cells and DCs, and axon development. In addition, CD47, by interacting with SIRPα, can inhibit the phagocytosis by macrophages. By emitting a "don't eat me" signal, CD47 protects normal cells, such as blood cells, from being attacked by macrophages.

Studies have shown that many tumor or cancer cells over-express CD47, which, by binding to the SIRPα on the cell surface of macrophages, prevent phagocytosis of the cancer cells by macrophages. This is deemed as one of the mechanisms adopted by tumors to evade the host's immune surveillance. Cancers that over-express CD47 include acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, and pancreatic cancer.

Other studies showed that injection of CD-47 specific antibody that blocks the binding of CD47 to SIRPα can significantly inhibit tumor growth in tumor-bearing mice. Tumor or cancer cells were eliminated completely when the same antibody was injected into the mice carrying human leukemia cells (Theocharides APA, et al., 2012).

An Fc receptor is a protein found on the surface of certain cells, including B lymphocytes, follicular dendritic cells, natural killer cells, macrophages, neutrophils, eosinophils, basophils, and mast cells. These cells contribute to the protective functions of the immune system. The Fc receptor binds to antibodies that are attached to infected cells, invading pathogens or cancer cells, and stimulates phagocytic or cytotoxic cells to destroy microbes, infected cells or cancer cells by antibody-mediated phagocytosis or antibody-dependent cell-mediated cytotoxicity.

The binding activity of SIRPα-Fc or SIRPαD1-Fc to CD47 has been reported (Lee W Y et al., 2007), but both having insufficient affinity to CD47.

SUMMARY OF THE INVENTION

The present invention discloses a recombinant fusion protein capable of eliminating tumors by i) blocking tumor cell induced production of inhibitory signals to macrophages, and ii) directly stimulating phagocytosis by macrophages. The fusion protein comprises a first extracellular Ig-like domain of human Signal-regulatory protein alpha (SIRPα) (SIRPαD1) linked to an Fc fragment of human IgG1 (SIRPαD1-Fc). The fusion protein is a homodimer having a molecular weight of 90 kDa, consisting of a first extracellular domain (Domain 1, D1) of SIRPα linked to an Fc fragment of human IgG (SIRPαD1-Fc). The fusion protein has a better binding activity to targets, compared to a recombinant protein containing the entire extracellular region of SIRPα (SIRPα-Fc). The present inventors have further discovered that the binding activity to targets can be further improved when the site for glycosylation in SIRPαD1 is removed (N89A); and the binding activity of Fc to Fc receptors may significantly improve SIRPαD1-Fc's anti-tumor activity.

A stably-expressing cell line of Chinese hamster ovary (CHO) cells has been obtained by screening, and proteins are produced by culturing the cell line in a shaking bed. In vitro experiments have shown that the protein of the present invention may bind to CD47 with an evidently improved binding activity compared to SIRPα-Fc. If the site for glycosylation "NIT" in SIRPαD1 is removed by genetic engineering (N89A) (SIRPαD1-Fc (N89A), designated as HY03M), the binding activity to CD47 is improved. In another aspect, when the $192^{th}$ amino acid residue in the Fc region is converted from aspartic acid to alanine (D192A) (SIRPαD1-Fc (N89A/D192A), designated as HY03MM), the binding activity to Fc receptors (CD16a, CD32, CD64) is evidently decreased. The in vivo anti-tumor effect of HY03M has been studied using human acute lymphoblastic leukemia and acute promyelocytic leukemia-carrying mouse models, indicating that HY03M has extremely good antitumor activity. Tumor growth is completely inhibited in mice treated by HY03M, and tumor is no longer detected in some mice. To confirm Fc's contribution to the anti-tumor activity, the in vivo therapeutic effects of HY03M and HY03MM have been tested in mice carrying human lymphoma in comparison to Rituximab. It turns out that HY03M has an evident anti-tumor effect compared to the negative control group, and its effect is also much better than Rituximab. Despite of a good inhibitory effect on tumor growth, HY03MM's activity is inferior to HY03M, suggesting that the Fc region is involved in tumor inhibition by binding to Fc receptors on macrophages.

In one embodiment, the recombinant protein of the present invention is HY03M (SEQ ID NO.: 5, SEQ ID NO.: 6). HY03M has a high anti-tumor activity, and inhibits tumor growth by i) blocking interaction between CD47 and SIRPα; and/or ii) activating macrophages by binding Fc to Fc receptors. HY03M may treat various CD47+ tumors.

The present invention also provides a nucleic acid molecule encoding the recombinant bi-functional fusion protein and an expression vector expressing the protein, a method for producing the protein and a method for treating a disease over-expressing CD47.

In one embodiment, the recombinant bi-functional fusion protein of the present invention comprises an extracellular Ig-like domain of Signal-regulatory protein (SIRP), linked to an Fc fragment of human IgG1, wherein the protein binds to CD47 to block the binding of CD47 to SIRP on the surface of macrophages so as to stimulate phagocytosis of tumor cells by macrophages.

In one embodiment, the signal-regulatory protein in the recombinant bi-functional fusion protein is SIRPα, and the extracellular Ig-like domain of the signal-regulatory protein is SIRPαD1.

In one embodiment, the recombinant bi-functional fusion protein of the present invention comprises an Fc fragment, a part of an immunoglobulin molecule. Although an Fc fragment does not have any antigen-binding site, but does stimulate effector functions. For example, the Fc fragment facilitates the binding of the antibody with Fc receptors or complement proteins. In one embodiment, the Fc fragment is an Fc fragment of IgG.

In one embodiment, the recombinant bi-functional fusion protein of the present invention comprises an amino acid sequence having at least 95% identity to SEQ ID NO.: 6. In one embodiment, the recombinant bi-functional fusion protein of the present invention comprises an amino acid sequence having at least 98% identity to SEQ ID NO.: 6. In one embodiment, the recombinant bi-functional fusion protein of the present invention comprises an amino acid sequence having at least 99% identity to SEQ ID NO.: 6. In one embodiment, the recombinant bi-functional fusion protein of the present invention comprises an amino acid sequence set forth in SEQ ID NO.: 6.

In one embodiment, the present invention provides a polynucleotide molecule encoding the recombinant bi-functional fusion protein of the present invention, wherein the recombinant bi-functional fusion protein comprises an extracellular Ig-like domain of signal-regulatory protein (SIRP), linked to an Fc fragment of human IgG1, wherein the protein binds to CD47 to block the binding of CD47 to SIRP on the surface of macrophages so as to stimulate phagocytosis of tumor cells by macrophages.

In one embodiment, the polynucleotide molecule of the present invention encodes a recombinant bi-functional fusion protein comprising SIRPα, preferably SIRPαD1.

In one embodiment, the polynucleotide molecule of the present invention encodes a recombinant bi-functional fusion protein comprising an Fc fragment of an Immunoglobulin, preferably an Fc fragment of human IgG1.

In one embodiment, the polynucleotide molecule of the present invention encodes a recombinant bi-functional fusion protein having an amino acid sequence that is at least 95% identical to SEQ ID NO.: 6. In one embodiment, the polynucleotide molecule of the present invention encodes a recombinant bi-functional fusion protein having an amino acid sequence that is at least 98% identical to SEQ ID NO.: 6. In one embodiment, the polynucleotide molecule of the present invention encodes a recombinant bi-functional fusion protein having an amino acid sequence that is at least 99% identical to SEQ ID NO.: 6. In one embodiment, the polynucleotide molecule of the present invention encodes a recombinant bi-functional fusion protein having an amino acid sequence set forth in SEQ ID NO.: 6.

In one embodiment, the present invention provides an expression vector comprising the polynucleotide molecule of the present invention, the polynucleotide molecule encoding a recombinant bi-functional fusion protein.

In one embodiment, the present invention provides a host cell comprising the expression vector of the present invention.

In one embodiment, the present invention provides a pharmaceutical composition, comprising the recombinant bi-functional fusion protein of the present invention, and at least one adjuvant.

In one embodiment, the present invention provides a method for treating a disease caused by over-expression of CD47, comprising administering to a patient or a subject a therapeutically effective amount of the pharmaceutical composition of the present invention.

In one embodiment, the present invention provides the use of the recombinant bi-functional fusion protein in the manufacture of a pharmaceutical composition for treatment of a disease caused by over-expression of CD47.

In one embodiment, the method of the present invention is for treating a disease selected from the group consisting of acute myelocytic leukemia (AML), chronic myelocytic leukemia (CML), acute lymphoblastic leukemia (ALL), non-Hodgkin's lymphoma (NHL), multiple myeloma (MM), Bladder cancer, ovarian cancer, prostate cancer, lung cancer, colon cancer, breast cancer, pancreatic cancer, and renal cell carcinoma. In one embodiment, the present invention provides a method for treating Crohn's disease, allergic asthma and rheumatoid arthritis.

DESCRIPTION OF THE DRAWINGS

FIG. 1A-1D is a schematic diagram of the structures and mechanism of action of SIRPs and SIRPαD1.

FIG. 2A-2B shows nucleic acid sequence and amino acid sequence of SIRPα-Fc.

FIG. 3A-3B shows nucleic acid sequence and amino acid sequence of SIRPαD1-Fc.

FIG. 4A-4B shows nucleic acid sequence and amino acid sequence of HY03M.

FIG. 5A-5B shows nucleic acid sequence and amino acid sequence of HY03MM.

FIG. 6A-6D shows SDS-PAGE analysis of four fusion proteins.

DETAILED DESCRIPTION OF THE INVENTION

Figure 7A:
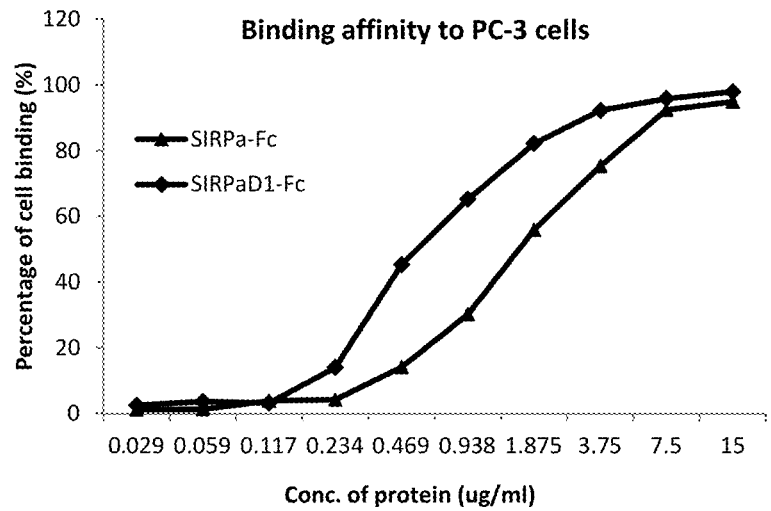
FIG. 7A-7B shows the binding activities of SIRPα-Fc and SIRPαD1-Fc to the targets on PC-3 cells, respectively.

The present invention is directed to a recombinant fusion protein, which can eliminate tumors via two approaches, i.e., to block tumor cell induced production of inhibitory signals to macrophages, and to directly stimulate the phagocytosis by macrophages. The protein consists of a first extracellular Ig-like domain of human Signal-regulatory protein alpha (SIRPα) (SIRPαD1) linked to an Fc fragment of human IgG1(SIRPαD1-Fc). The fusion protein is a homodimer having a molecular weight of 90 kDa. A stably-expressing cell line of Chinese hamster ovary (CHO) cells has been obtained by screening, and 100 mg of the proteins are produced by culturing the cell line in a shaking bed. In vitro experiments have shown that the proteins may bind to CD47 with an evidently improved binding activity compared to SIRPα-Fc. If the site for glycosylation ("NIT") in SIRPαD1 is removed by genetic engineering (N89A) (SIRPαD1-Fc (N89A), designated as HY03M), the binding activity to CD47 will be improved. In another aspect, when the 211$^{th}$ amino acid residue in the Fc region is converted from aspartic acid to alanine (D192A) (SIRPαD1-Fc (N89A/ D192A), designated as HY03MM), the binding activity to Fc receptors (CD16a, CD32, CD64) is evidently decreased. The in vivo anti-tumor effect of HY03M has been studied using human acute lymphoblastic leukemia and acute pro-myelocytic leukemia-carrying mouse models, indicating that HY03M has extremely good anti-tumor activity. Tumor growth is completely inhibited in mice treated by HY03M, and tumor is no longer detected in some mice. To confirm Fc's contribution to the anti-tumor activity, in vivo therapeutic efficacies of HY03M and HY03MM have been tested in mice carrying human lymphoma in comparison to Rituximab. It turns out that HY03M has an evident anti-tumor effect compared to the negative control group, and its effect is also much better than Rituximab. Despite of a good inhibitory effect on tumor growth, HY03MM's activity is inferior to HY03M, suggesting that the Fc region is involved in tumor inhibition by binding to Fc receptors distributed on macrophages.

The fusion protein of the present invention contains two fragments, i.e., the target-binding fragment (SIRPαD1) and the Fc fragment.

The recombinant bi-functional fusion protein of the present invention may further bind to non-polypeptide molecules for the purpose of conferring desired properties such as reducing degradation and/or increasing half-life, reducing toxicity, reducing immunogenicity, and/or increasing the biological activity. Exemplary molecules include but are not limited to polymers such as polyethylene glycol (PEG), polylysine, a dextran; a lipid; a cholesterol group (such as a steroid); a carbohydrate, or an oligosaccharide molecule.

The Fc fragment may be 232 amino acids in size, and comprises a cystein in the hinge region, two cysteins in the CH2 region and two cysteins in the CH3 region. The cystein in the hinge region contributes to the formation of disulfide bond between two monomers, thereby generating a homodimer, while the cysteins in the CH2 and CH3 regions can form intrachain disulfide bonds to stabilize the protein.

For example, the extracellular Ig domain of SIRP (SIRPα, SIRPγ) capable of binding CD47 can be used in the fusion protein.

Preferably, human-derived sequences may be used in human cancer therapies, as the strong immunogenicity of the proteins or peptides from non-human animals may lead to allergy and other adverse effects. However, other animal proteins or peptides may also be used in the present invention based on different application purposes.

In one embodiment, the signal-regulatory protein in the recombinant bi-functional fusion protein of the present invention is SIRPα. The extracellular Ig-like domain of the signal-regulatory protein is SIRPαD1.

In the present invention, the Fc fragment from any immunoglobulin can be used. Immunoglobulins include IgG, IgA, IgM, IgD and IgA, among which IgG is the most abundant and relatively stable. The Fc fragment of IgG, the Fc fragment of IgG1 and the Fc fragment of human IgG1 are preferred in the present invention as these Fc fragments exhibit the highest binding activity with staphylococcus Protein A and therefore can be easily purified.

In one embodiment, the recombinant bi-functional fusion protein of the present invention comprises a first extracellular Ig-like domain of human SIRPα, linked to an Fc fragment of human IgG.

In one embodiment, the amino acid sequence of the recombinant bi-functional fusion protein of the present invention is shown in FIG. 4B (SEQ ID NO.: 6). In another embodiment, the polypeptide has an amino acid sequence set forth in SEQ ID NO.: 6. In another embodiment, the polypeptide has an amino acid sequence with at least 80%, 85%, 90%, 95%, 98% or 99% identity to SEQ ID NO.: 6, wherein the polypeptide is capable of binding to CD47 and is able to inhibit tumor cell growth.

In another aspect, the present invention provides an isolated nucleic acid molecule comprising a polynucleotide encoding a recombinant bi-functional fusion protein, wherein, the recombinant bi-functional fusion protein comprises a polypeptide having the sequence set forth in SEQ ID NO.: 6. In one embodiment, the polypeptide has an amino acid sequence having at least 80%, 85%, 90%, 95%, 98% or 99% identity to SEQ ID NO.: 6, wherein the polypeptide is capable of binding to CD47 and is able to inhibit tumor cell growth.

The present invention also discloses a pharmaceutical composition comprising the aforementioned recombinant bi-functional fusion protein, and at least one pharmaceutically acceptable excipient. If needed, one or more pharmaceutically acceptable carriers or excipients may also be included in the pharmaceutical composition. The carriers include diluents, excipients, bulking agents, bonding agents, wetting agents, disintegrating agents, absorption enhancers, surfactants, sorption carriers, lubricants and the like ordinary in the pharmaceutics.

Such compositions comprise a therapeutically or prophylactically effective amount of the polypeptide or protein in admixture with pharmaceutically acceptable materials, and physiologically acceptable formulation materials. The pharmaceutical composition may contain formulation materials for modifying, maintaining or preserving, for example, the pH, osmolarity, viscosity, clarity, color, odor, sterility, isotonicity, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, ammonium bicarbonate, Tris-HCl, citrates, phosphates, and other organic acids); bulking agents (such as mannitol or glycine), chelating agents (such as ethylenediamtne tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring agents; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as PLURONICS® or poloxamers, PEG, sorbitan esters, polysorbates such as polysorbate 20, polysorbate 80, TRITON® X (Polyethylene glycol p-(1,1,3,3-tetramethylbutyl)-phenyl ether), tromethamine, lecithin, cholesterol, tyloxapal); stability enhancing agents (sucrose or sorbitol); tonicity enhancing agents (such as alkali metal halides, preferably sodium or potassium chloride, mannitol sorbitol); delivery vehicles; diluents; excipients and/or pharmaceutical adjuvants.

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection and physiological saline solution.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in injection. For example, the vehicle or carrier may be neutral buffered saline or saline mixed with serum albumin. Other exemplary pharmaceutical compositions comprise Tris buffers, or acetate buffers, which may further include sorbitol or a suitable substitute thereof. In one embodiment of the present invention, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

The formulations can be delivered in a variety of methods, for example, by inhalation therapy, orally, or by injection. When parenteral administration is contemplated, the therapeutic compositions for use in this invention may be in the form of a parenterally acceptable aqueous solution comprising the desired polypeptide in a pharmaceutically acceptable vehicle. A particularly suitable vehicle for parenteral injection is sterile distilled water in which a polypeptide is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. Inhalation solutions may also be formulated with a propellant for aerosol delivery, in yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the therapeutic molecule. Diluents, flavorings, low melting point waxes, vegetable oils, lubricants, suspending agents, tablet disintegrating agents, and binders may also be employed. Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arable and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Additional pharmaceutical compositions will be evident to those skilled in the art, including formulations involving polypeptides in sustained- or controlled-delivery formulations. Techniques for formulating a variety of other sustained- or controlled-delivery means, such as liposome carriers, bio-erodible micro-particles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (Langer et al, J. Biomed. Mater. Res., 15: 167-277, (1981); Langer et al., Chem. Tech., 12:98-105 (1982)), ethylene vinyl acetate (Langer et al., supra) or poly-D(–)-3-hydroxybutyric acid (EP 133,988). Sustained-release compositions also include liposomes, which can be prepared by any of several methods known in the art. See e.g., Eppstein et al., PNAS (USA), 82:3688 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. Tine composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebro ventricular, intramuscular, intra-ocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, the bi-functional fusion protein of the present invention can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semipermeable polymeric enclosures or membranes that allow the release of the polypeptide product(s) but prevent the destruction of the cells by the patient's immune system or by other detrimental factors from the surrounding tissues.

A gene therapy in vivo is also envisioned wherein a nucleic acid molecule encoding the bi-functional fusion protein of the present invention, or a derivative thereof is introduced directly into the subject. For example, a nucleic acid sequence encoding a bi-functional fusion protein of the present invention is introduced into target cells via local injection of a nucleic acid construct with or without an appropriate delivery vector, such as an adeno-associated virus vector. Alternative viral vectors include, but are not limited to, retroviruses, adenovirus, herpes simplex vims and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present invention is to provide a method for preparing the above recombinant bi-functional fusion protein and the pharmaceutical composition comprising the same. In one embodiment, the method comprises (1) providing an protein-encoding polynucleotide molecule; (2) constructing an expression vector comprising the polynucleotide molecule of (1); (3) transfecting or transforming suitable host cells with the expression vector of (2) and cultivating the host cells to express the protein; and (4) purifying the protein. The preparation may be carried out with well-known technologies by an ordinarily skilled artisan.

Another object of the present invention is to provide a method of treating cancer using the pharmaceutical composition of the present invention, comprising administrating an effective amount of the aforementioned pharmaceutical composition to the patients or subjects in need thereof. In one embodiment, the pharmaceutical composition is used to treat CD47-overexpressing tumors or cancers, including but not limited to acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, pancreatic cancer and renal cancer.

In one embodiment, the diseases related to over-expression of CD47 include but are not limited to Crohn's disease, allergic asthma, and rheumatoid arthritis.

Also, the present invention provides a polynucleotide molecule encoding the recombinant bi-functional fusion protein and an expression vector expressing the recombinant bi-functional fusion protein. Examples of vectors include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

The present invention provides host cells comprising the above expression vectors. The host cells may be transformed or transfected with the expression vectors. Suitable host cells include *Escherichia coli*, yeasts and other eukaryotes. Preferably, *Escherichia coli*, yeast or mammalian cell lines (such as COS or CHO) are used.

The present invention is now further described with the non-limiting examples below.

EXAMPLES

Example 1

Method and Material 1.1 Construction of Vectors Expressing SIRPα-Fc and SIRPαD1-Fc Respectively Plg-Tail (R&D Systems) was employed as the expression vector. The coding sequences of extracellular domains of SIRPα and SIRPαD1 were amplified from THP-1 (ATCC®TIB-202™) cells, respectively, using primer 1 (SEQ ID NO.: 9) with primer 2 (SEQ ID NO.: 10), and primer 1 (SEQ ID NO.: 9) with primer 3 (SEQ ID NO.: 11). The PCR products were cloned into HindIII/EcoRI site in an engineered Plg-Tail, thus generating pSIRPα-Fc and pSIRPαD1-Fc expression vectors.

1.2 Construction of Vectors Expressing HY03M and HY03MM Respectively

The coding sequence of SIRPαD1 having N89A mutation was synthesized by Nanjing Jinsirui biotechnology Co., Ltd (Program NO.: 7009323-1) and then cloned into HindIII/EcoRI site of Plg-Tail vector to generate an HY03M expression vector. Using primer 4 (SEQ ID NO.: 12) and primer 5 (SEQ ID NO.: 13), the nucleotide sequence (GAC) encoding aspartic acid, the 192th amino acid residue of HY03M at the Fc terminus, was mutated to encode alanine (GCC) through site-directed mutagenesis, thus generating an HY03MM expression vector.

TABLE 1

PCR primers

| Primer No. | Primer sequences (5'-3') | Gene | Endo-nuclease |
|---|---|---|---|
| Primer 1: | CCC<u>AAGCTT</u>GGGGCCACC*ATGGAGCCCGCCGGCCCGGCCC* (SEQ ID No.: 9) | SIRPα | HindIII |
| Primer 2: | CG<u>GAATTC</u>*GTTCCGTTCATTAGATCCAGTG* (SEQ ID No.: 10) | SIRPα | EcoRI |
| Primer 3: | CG<u>GAATTC</u>*GTGCTGAGGTGTGGCCCTCGCC* (SEQ ID No.: 11) | SIRPα | EcoRI |
| Primer 4: | GAGGTCACATGCGTGGTGGTGGCCGTGAGCCACGAAGACCCTG (SEQ ID No.: 12) | hIgG1-Fc | |
| Primer 5: | CACCACCACGCATGTG ACCTCAGGGGTCCGGGAGATCATG (SEQ ID No.: 13) | hIgG1-Fc | |

Notes:
Gene specific sequences were shown in italic, and endonuclease recognition sites were underlined.

2. Protein Expression and Purification

The complete cell culture media DMEM (with 10% FBS) containing CHO cells was added into a 24-well plate, 0.5 ml per well, and the plate was kept in an incubator for 24 hours. For transfection, 0.5 μg of plasmid DNA and 2 μl of LIPOFECTAMINE™ 2000 (Cat #11668-027, invitrogen) were separately dissolved in 50 μl of serum-free culture media, which were then combined and left still at room temperature for 20 minutes. Thereafter, the medium was slowly poured into wells of the plate, and the plate was placed in the incubator for 24 hours. On the next day, 100 μl of supernatant was taken and tested for protein expression by enzyme-linked immunosorbent assay (ELISA).

3. Protein Expression Assay

Protein expression was tested by ELISA. In particular, an goat anti-human IgG antibody, F(ab')2 fragment (Biosource international Inc) was dissolved in PBS buffer, which was then added into a 96-well ELISA plate, 20 ng per well. The ELISA plate was placed in a refrigerator at 4° C. overnight. Upon testing, the plate was blocked with blocking solution (PBS, 0.05% TWEEN®20 (polysorbate 20), 3% skim milk) for 1 hour, and then added with diluted serum and incubated for 1 hour at room temperature. After washed with a washing solution (PBS, 0.05% TWEEN®20 (polysorbate 20)) for 5 times, the plate was added with horse radish peroxidase (HRP) labeled rabbit anti-human IgG antibody (Jackson ImmunoResearch Lab) and was incubated at room temperature for 1 hour. After washed for 5 times, the substrate for HRP was added. Two minutes later, the solution (1N $H_2SO_4$) for stopping color development was used to terminate the chromogenic reaction. The optical density was measured at 450 nm.

4. Screening for Stably-Expressing Cell Line

Transfected cells were subjected to concentration-increasing antibiotic screening (GENETICIN®) (G-418), Cat #10131035, Invitrogen). The unstable cells were killed gradually, and survived cells were diluted and put into five 96-well plates, 0.5 to 1 cell per well. The plates were placed in an incubator for 10-15 days. The wells each containing a single clone were tested by ELISA, and then the cells with positive protein expression were propagated, and habitually cultured with serum-tree EX-CELL® CD CHO culture media (Cat #14361C-1000ML, SIGMA). After further screening, the cells with the highest expression levels were selected and frozen for use.

5. Protein Production and Purification

The stably-expressing cell line ($3 \times 10^5$/ml) was inoculated into a 2 L shake flask containing 300 ml of serum-free culture medium, and the shake flask was placed in a shaking bed for culture. After a cell density of $5 \times 10^6$/ml was reached, the supernatant was collected. The supernatant was purified using Protein A column. The purified protein was transferred to PBS (pH 7.0) with dialysis. Protein electrophoresis was employed to provide proteins having a purity of at least 98%.

6. Target Binding Activity

The binding activities of SIRPα-Fc, SIRPαD1-Fc, and HY03M to CD47 were tested by using flow cytometry.

Two cell lines, PC-3 (human prostate cancer) and Jurkat (T lymphocyte leukemia), were used to test the binding activity of each protein to CD47. After washed with PBS, the cells were suspended in PBS with a concentration of $1 \times 10^6$/ml. The cell suspension was added with hIgG (1 μg/ml) and then incubated in a refrigerator at 4° C. for 1 hour. After washes with PBS, the cells were transferred to a 96-well U-shaped cell culture plate (Cat #163320, NUNC), 100 μl per well. Then, the cells were added with purified proteins with different oncentrations and then incubated in a refrigerator at 4° C. for 1 hour. The cells were washed with and then suspended in PBS. Thereafter, the cells were incubated together with FITC-labeled anti-human IgG-Fc antibody (Cat # F9512, Sigma). After 1 hour, the cells were tested in a flow cytometry (Guava easyCyte 6HT-2L, Millipore).

7. Target Blockade Assay

In order to test whether the purified proteins can block the binding of CD47 to SIRPα, FITC-labeled SIRPα-Fc (Cat #4546-SA-050, R&D Systems, 100 nM) was mixed with unlabeled SIRPα-Fc, SIRPαD1-Fc, HY03M, HY03MM or hIgG-Fc of different concentrations. Then, each mixture was put in a 96-well U-shaped plate with Jrukat cells, and incubated in a refrigerator at 4° C. for 1 hour. After washes with PBS, the cells were re-suspended in 200 ml of PBS and analyzed for the ratio of fluorescent cells in a flow cytometry.

8. Binding to FcγRs

The binding activities of proteins of the present invention to FcγRs were tested by ELISA as follows.

CD64 (FcγRI) (Cat: 1257-FC-050, R&D Systems), CD32a (FcγRIIa) (Cat: 1330-CD-050/CF, R&D Systems), CD32b (FcγRIIb) (Cat: 1875-CD-050, R&D Systems), and CD16a (FcγRIIIa) (Cat: 4325-FC-050, R&D Systems) were diluted with a coating buffering solution (CBS) (Sigma-Aldrich Co., Product code: 1001329288 C3041-100CAP) to a concentration of 1000 ng/ml, and 100 μl of each solution was added into an ELISA plate (Cat #442404, Nunc™), 100 ng per well. The plate was left in a refrigerator at 4° C. overnight. Immediately before the test, the plate was washed by 0.05% PBS-T and then blocked by 3% skim milk for 1 hour at room temperature. The diluted solutions of HY03M and HY03MM (800, 400, and 200 nM) were added into the plate, 100 μl per well. After incubated at room temperature for 1 hour, the liquids in the plate were discarded. The plate was washed by 0.05% PBS-T for 5 times, and then added with 100 μl of HRP-Rabbit anti-human IgG Fc (Cat #: 309-036-008, Jackson ImmunoResearch Lab) diluted at 1:20000. The plate was incubated at room temperature for 1 hour and then washed by the washing solutions for 5 times. Thereafter, HRP substrates were added to the plate, and the plate was left for colorimetric reaction for 10 to 20 minutes in the dark. The colorimetric reaction was terminated later using 1 N $H_2SO_4$, and the OD450 value was obtained in a plate reader.

9. Phagocytosis Assay

Mouse macrophages (Raw264.7) were added into a 96-well plate, $5 \times 10^5$ cells per well, and incubated for 2 hours in an incubator at 37° C. Jurkat cells labelled with CFSE (2.25 μM) were incubated with 2.5 μg/ml HY03M, HY03MM or IgG-Fc for 30 minutes at 37° C. and then transferred to the plate containing Raw264.7 macrophages mentioned above. The plate was incubated at 37° C. for another 3 hours. With washes by PBS for 3 times, Jurkat cells free in the solution were removed. The Raw264.7 cells were then observed in a flow cytometry through the CFSE contained in these cells.

10. Antitumor Assay

The in vivo antitumor activity of HY03M was studied in a HL-60 subcutaneous tumor model. Twenty Balb/c nude mice were injected subcutaneously with leukemia (HL60) cells, $4 \times 10^6$ cells per mouse. When the tumors grew up to 100 to 150 $mm^3$ in volume, the mice were randomly divided into 3 groups. The first group was intraperitoneally injected with PBS, while the second group was intraperitoneally injected with a VEGF inhibitor. The third group was intraperitoneally injected with HY03M. Each group was administered with said agent for 6 times at a dose of 10 mg/kg, twice a week. The volume and weight of the tumors were measured twice a week.

In order to know whether the Fc region contributed to anti-tumor effect, the anti-tumor activities of HY03M and HY03MM were tested using a lymphoma model, respectively, in comparison with Rituximab. Thirty-eight Balb/c rude mice were subcutaneously injected with Daudi cells, $1 \times 10^7$ cells per mouse. When the tumors grew up to 100 to 150 $mm^3$ in volume, the mice were randomly divided into 5 groups. The first group was intraperitoneally injected with PBS, while the second to fifth group were intraperitoneally injected with HY03M, HY03MM, Rituximab, and HY03MM plus Rituximab, respectively. Each group was administered with said agent for 8 times at a dose of 5 mg/kg, twice a week. The volume and weight of the tumors were measured twice a week.

Experimental Results

1. Construction of Expression Vectors

The structure of SIRPαD1-Fc was shown in FIG. 1B and FIG. 1D, wherein SIRPαD1 was linked to the N-terminus of IgG1-Fc. The nucleic acid sequence and amino acid sequences of each protein were shown in FIG. 2 to FIG. 5. The coding sequence of SIRPα-Fc consisted of 1752 nucleotides (FIG. 2A, SEQ ID No.: 1), encoding 583 amino acids (FIG. 2B, SEQ ID No.:2). Among the 1752 nucleotides, 1047 encoded SIRPα, 696 encoded Fc, and the remaining 6 formed EcoRI site. The coding sequence of SIRPαD1-Fc consisted of 1131 nucleotides (FIG. 3A, SEQ ID No.:3), encoding 376 amino acids (FIG. 3B, SEQ ID No.:4), wherein, 426 nucleotides encoded SIRPαD1, 696 encoded Fc, and the remaining 6 formed EcoRI site. HY03M and HY03MM contained 1125 nucleotides, wherein HY03M had a N89A mutation (FIGS. 4A and 4B, SEQ ID No.:5 and 6), while HY03MM contained a N89A mutation and a D192A mutation (FIGS. 5A and 5B, SEQ ID No.:7 and 8).

2. Protein Expression Analysis

Theoretically, the four proteins, SIRPα-Fc, SIRPαD1-Fc, HY03M and HY03MM, had molecular weights of ~128 kDa, ~82.7 kD, ~82.3 kDa and ~82.3 kDa, respectively. With protein electrophoresis (SDS-PAGE), it was found that all the molecular weights were larger than the theoretically predicted ones under non-reducing conditions (FIG. 6), which might be due to protein glycosylation at a glycosylation site in relation to an Asn residue in SIRPαD1. The irregular glycosylation at this site may lead to the presence of two bands on SDS-PAGE gel under non-reducing conditions (FIG. 6B). If the site for glycosylation was removed, as in HY03M and HY03MM, only one band was found instead of two (FIGS. 6C and 6D).

3. Target Binding Activity Assay

Figure 7B:
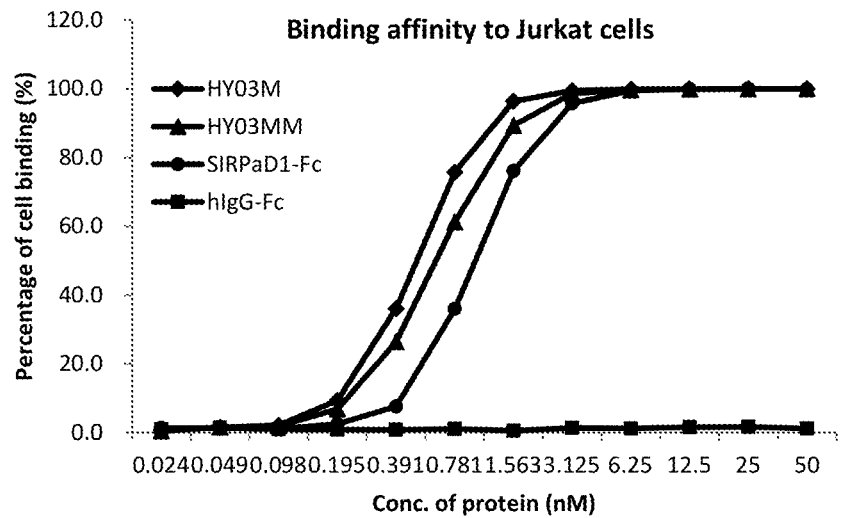

By using flow cytometry, the binding activities of SIRPα-Fc and SIRPαD1-Fc to PC-3 cells were analyzed (FIG. 7A). It was found that the binding activity of SIRPαD1-Fc (EC50=6.57 nM) was significantly higher than that of SIRPα-Fc (EC50=12.63 nM). As previous studies showed that the glycosylation had no effect on binding of D1 to CD47 (Lee W Y et al., 2007), N89 in D1 region was mutated to A (the protein variant was designated as HY03M). The binding activity of HY03M to CD47 was compared with that of SIRPαD1-Fc. The result indicated that HY03M with the glycosylation site removed had an evidently higher binding activity to targets (EC50=0.5 nM) than SIRPαD1-Fc (EC50=1.0 nM), as shown in FIG. 7B. The study here suggested that the protein containing only D1 region had a better target binding activity than the protein containing whole extracellular domains, and to remove the glycosylation site in D1 further promoted the binding activity (the target binding activity: HY03M>SIRPαD1-Fc>SIRPα-Fc).

4. Target Blockade Assay

Figure 8:
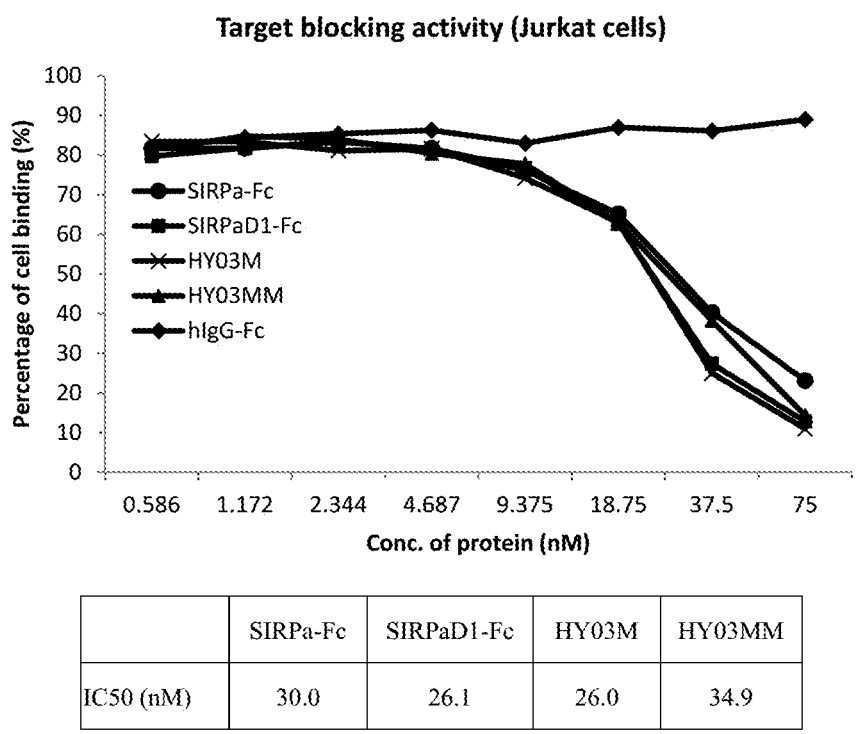
FIG. 8 shows the blockade of fluorescently labeled targets by unlabeled proteins.

With flow cytometry, the effect of the unlabeled proteins, SIRPα-Fc, SIRPαD1-Fc, HY03M and HY03MM, on binding of fluorescently labelled SIRPα-Fc with targets was studied. The results showed that, as in FIG. 8, these four proteins can all block binding of the fluorescently labelled protein to the target Jrukat cells in a dose dependent manner, with SIRPαD1-Fc and HY03M having the best blockade effects (see the table on lower part of FIG. 8).

Figure 9A:
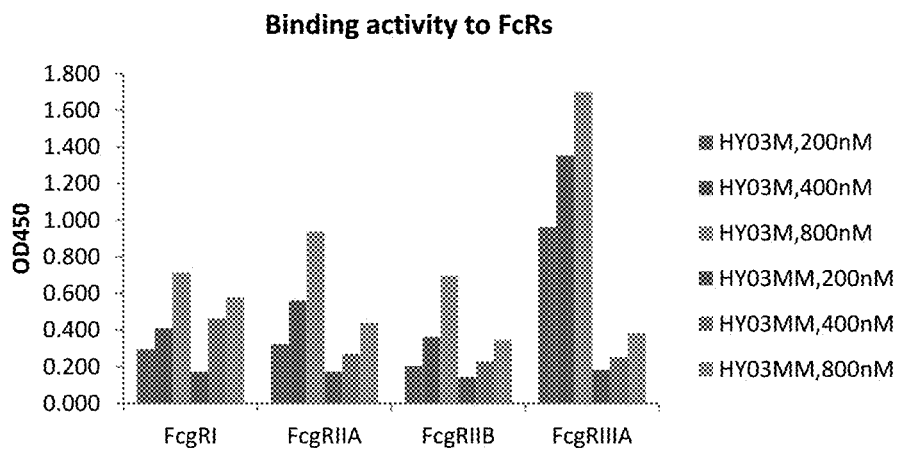
FIG. 9A-9B shows the binding activity to Fc receptors and the induced phagocytosis of tumor cells by macrophages.

5. Effect of Binding Activity of HY03M or HY03MM with FcγRs on Phagocytosis by Macrophages The $265^{th}$ amino acid residue of human IgG1-Fc, aspartic acid (D), was key to antibody's function. If aspartic acid was converted to alanine (D265A), IgG would lose its binding activity to FcγRs (FcγRI, FcγRIIA, FcγRIIB, FcγRIIIA) (Shields R L, et al., 2001) and the corresponding ADCC, CDC and the like. To confirm whether Fc part in HY03M contributed to the anti-tumor activity, the aspartic acid in Fc region of HY03M was converted to alanine (HY03MM, D192A, FIG. 5B), and the binding activity of HY03M to FcγRs (FcγRI, FcγRIIA, FcγRIIB, FcγRIIIA) was analyzed in comparison with HY03MM. The results showed that, as in FIG. 9A, the binding activity of the protein variant (HY03MM) to FcγRs was decreased significantly, especially the binding activity to FcγRIIA, FcγRIIB and FcγRIIIA.

Figure 9B:
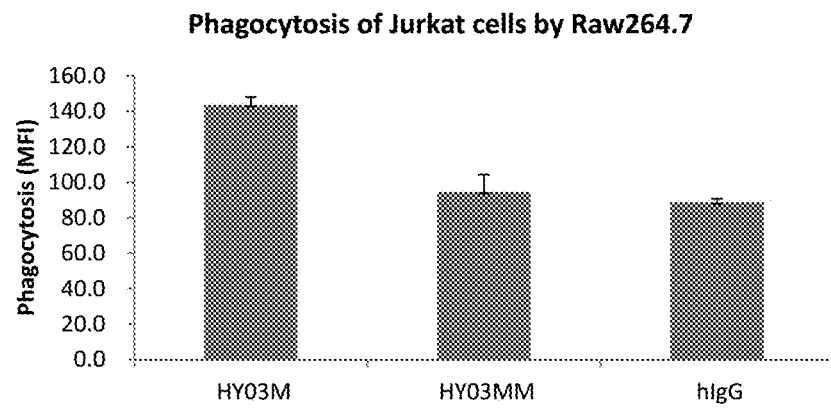

To test the effect of the amino acid residue mutation on macrophages' activities, fluorescently (CFSE) labelled target Jurkat cells were incubated together with macrophages (Raw264.7) and HY03M or HY03MM. It turned out that HY03M evidently promoted the phagocytosis by macrophages as compared to the negative control group (IgG), and HY03MM lost such a function and showed no difference when compared to IgG, as shown in FIG. 9B.

The study suggested that the blockade of CD47-SIRPα binding by, for instance, HY03MM, was not sufficient to induce phagocytosis of target cells by macrophages. The interaction between Fc and FcγRs on surfaces of macrophages, when combined with the blockade of CD47-SIRPα binding, will stimulate phagocytosis.

6. In Vivo Anti-Tumor Activities of HY03M and HY03MM

Figure 10A:
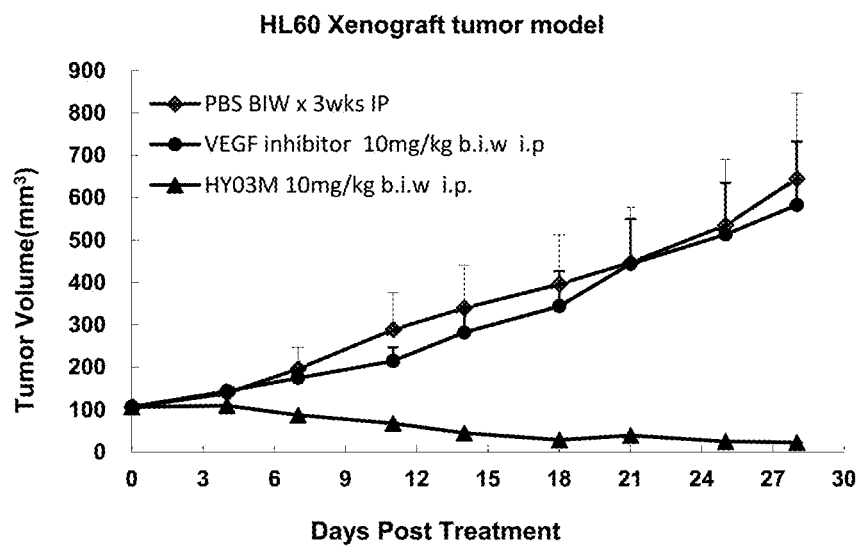
FIG. 10A-10B shows the in vivo therapeutic efficacies of four fusion proteins on tumors, respectively.

The in vivo anti-tumor activity of HY03M was studied in a HL-60 subcutaneous tumor model. As shown in FIG. 10A, after treated by the VEGF inhibitor, tumor growth was not evidently inhibited in tumor-bearing mice. In the group with HY03M treatment, tumor growth was significantly inhibited, wherein the tumor size decreased gradually from 100 $mm^3$ at the beginning of treatment, and almost vanished at the end of the experiment. In the negative control group, tumor size increased over time and became 1000 $mm^3$ at the end of the experiment. The results suggested that the activity inhibition of VEGF alone had no obvious treatment effect on HL60 tumor, indicating that the growth of HL60 tumors did not depend much on VEGFs. However, if the inhibitory effect on phagocytosis by macrophages was removed, phagocytosis of tumor cells by macrophages would be promoted, eliminating tumor cells.

Figure 10B:
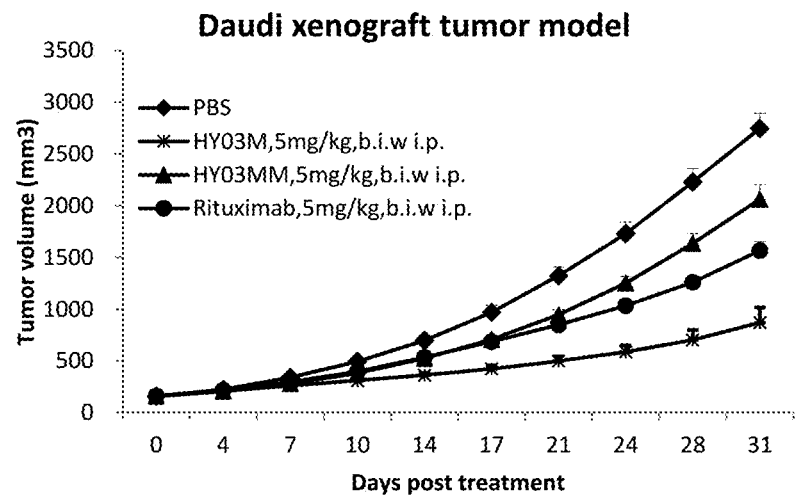

To test whether the Fc region was involved in HY03M's anti-tumor activity, the therapeutic effects of HY03M, HY03MM and Rituximab on lymphoma were studied using a lymphoma (Daudi) model. It can be seen (FIG. 10B) that tumor growth was significantly inhibited in the group with HY03M treatment (TGI=72.5%), which was much better than that in Rituximab group (TGI=45.6%). However, HY03MM with Fc region having a mutation had a much attenuated inhibitory effect on tumor growth (TGI=26.4%), suggesting that Fc region was involved in HY03M's anti-tumor activity.

The above data indicated that HY03M treated tumors by i) inhibiting binding of CD47 with SIRPα so that the inhibitory signals transmitted by SIRPα were blocked and macrophages were activated; and ii) binding Fc to FcγRs to active macrophages.

CONCLUSIONS

Our studies indicated that the recombinant protein SIRPαD1-Fc had a good target binding activity which was better than that of SIRPα-Fc. If the site for glycosylation was removed, as in HY03M, the target binding activity was further improved. In vivo studies showed that HY03M had a good anti-tumor activity, and would completely eliminate tumors in HL60 model. The protein fought tumors by i) inhibiting binding of CD47 with SIRPα so that the inhibitory signals transmitted by SIRPα were blocked and macrophages were activated; and ii) binding Fc to FcγRs to active macrophages. The two mechanisms produced a synergistic effect, sufficiently stimulating phagocytosis of tumor cells by macrophages. The activated macrophages may further present tumor antigens to T lymphocytes (Tseng D, et al., 2013) and kill the tumor cells finally.

As described above, for the binding activity of SIRPα-Fc or SIRPαD1-Fc to CD47, it was once reported (Lee W Y et al., 2007) that the affinities of these two proteins to CD47 were not different. Our studies here showed that the affinity of SIRPαD1-Fc to CD47 (in PC-3 cells) (EC50=6.57 nM) was much higher than that of SIRPα-Fc (EC50=12.63 nM). With amino acid analysis, it was found that SIRPαD1-Fc had 9 more amino acid residues (SCAWSGVAG (SEQ ID NO.: 14)) at the N-terminus compared to that constructed by Lee W Y et al., which might contribute to the increased target binding activity. Further studies found that the target binding activity was further improved when the glycosylation site (N89A) in D1 region was removed. In addition, with site-directed mutagenesis (D192A) in Fc region, Fc was found to help protein purification (by Protein A chromatography) and to improve protein stability, and also be involved in HY03M's anti-tumor activity, as the anti-tumor activity of the variant protein with D192A was greatly decreased.

While the invention has been described above in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

REFERENCES

1. Gardai S J, McPhillips K A, Frasch S C, Janssen W J, Starefeldt A, Murphy-Ullrich J E, Bratton D L, Oldenborg P A, Michalak M, Henson P M. Cell-surface calreticulin initiates clearance of viable or apoptotic cells through trans-activation of LRP on the phagocyte. Cell. 2005; 123:321-334.
2. Obeid M, Panaretakis T, Joza N, Tufi R, Tesniere A, van Endert P, Zitvogel L, Kroemer G. Calreticulin exposure is required for the immunogenicity of gamma-irradiation and UVC lightinduced apoptosis. Cell Death Differ. 2007; 14:1848-1850.
3. Orr A W, Pedraza C E, Pallero M A, Elzie C A, Goicoechea S, Strickland D K, Murphy-Ullrich J E. Low density lipoprotein receptor-related protein is a calreticulin coreceptor that signals focal adhesion disassembly. J Cell Biol. 2003; 161:1179-1189.
4. Theocharides. A. P. A.; Jin L. Q.; Chenge P. Y.; Prasolava, T. K.; Malko. A. V.; Ho. J. M.; PoeDl. A. G.; Rooiien. N. van; Minden. M. D.; Danska. J. S.; Dick J.; Wang J. C. Y. J. Exp. Med. 2012 Vol. 209 No. 10 1883-1899
5. Lee W Y et al. Novel Structural Determinants on SIRPα that Mediate Binding to CD47. *J Immunol* 2007; 179: 7741-7750.
6. Shields R L et al. High Resolution Mapping of the Binding Site on Human IgG1 for FcγRI, FcγRII, FcγRIII, and FcRn and Design of IgG1 Variants with Improved Binding to the FcgR. JBC. 2001, 276:6591-6604.
7. Tseng D, et al. Anti-CD47 antibody-mediated phagocytosis of cancer by macrophages primes an effective anti-tumor T-cell response. PNAS. 2013, 110:11103-11108

What is claimed is:

1. A recombinant bi-functional fusion protein, comprising an extracellular Ig-like domain of a signal-regulator protein (SIRP), linked to an Fc region of an immunoglobulin comprising both CH2 and CH3 regions of the immunoglobulin, wherein the signal-regulatory protein is SIRPα, the extracellular Ig-like domain of the signal-regulator protein is, and the SIRPαD1 has mutation N89A and consists of the amino acid sequence from residue 1 to 142 of SEQ ID NO.: 6, wherein the recombinant bi-functional fusion protein can bind to Cluster of Differentiation 47 (CD47) and Fcγ Receptor, blocking the binding of CD47 to the SIRP on the cell surface of macrophages and stimulating phagocytosis of tumor cells by macrophages.

2. The recombinant bi-functional fusion protein of claim 1, wherein the Fc region is an Fc region of IgG1.

3. The recombinant bi-functional fusion protein of claim 2, wherein the IgG1 is a human IgG1.

4. A homodimer comprising two recombinant bi-functional fusion proteins of claim 1 linked by one or more disulfide bonds.

5. The recombinant bi-functional fusion protein of claim 3, wherein the Fc region comprises an amino acid sequence having at least 95% identity to the amino acid sequence set forth in SEQ ID NO: 6 from residue 143 to residue 374.

6. The recombinant bi-functional fusion protein of claim 3, wherein the Fc region comprises an amino acid sequence having at least 98% identity to the amino acid sequence set forth in SEQ ID NO: 6 from residue 143 to residue 374.

7. The recombinant bi-functional fusion protein of claim 3, wherein the Fc region comprises an amino acid sequence having at least 99% identity to the amino acid sequence set forth in SEQ ID NO: 6 from residue 143 to residue 374.

8. The recombinant bi-functional fusion protein of claim 5, wherein the Fc region consists of the amino acid sequence from residue 143 to residue 374 of SEQ ID NO.: 6.

9. The recombinant bi-functional fusion protein of claim 8, comprising the amino acid sequence set forth in SEQ ID NO.: 6.

10. The recombinant bi-functional fusion protein of claim 9, consisting of the amino acid sequence set forth in SEQ ID NO.: 6.

11. The homodimer of claim 4, wherein the Fc region is an Fc region of IgG1.

12. The homodimer of claim 11, wherein the IgG1 is a human IgG1.

13. The homodimer of claim 12, wherein the Fc region consists of the amino acid sequence from residue 143 to residue 374 of SEQ ID NO.: 6.

* * * * *

UNITED STATES PATENT AND TRADEMARK OFFICE
CERTIFICATE OF CORRECTION

PATENT NO. : 10,800,821 B2
APPLICATION NO. : 15/566724
DATED : October 13, 2020
INVENTOR(S) : Wenzhi Tian et al.

Page 1 of 1

It is certified that error appears in the above-identified patent and that said Letters Patent is hereby corrected as shown below:

In the Claims

Column 33:
Claim 1, Line 48 and Line 52, "signal-regulator" should be --signal-regulatory--
Claim 1, Line 53, after is, insert --SIRPαD1--

Signed and Sealed this
Third Day of May, 2022

Katherine Kelly Vidal
*Director of the United States Patent and Trademark Office*

SEQUENCE LISTING

<160> NUMBER OF SEQ ID NOS: 14

<210> SEQ ID NO 1
<211> LENGTH: 1752
<212> TYPE: DNA
<213> ORGANISM: Homo sapiens

<400> SEQUENCE: 1

```
tcctgcgcct ggtcaggagt ggcgggtgag gaggagctgc aggtgattca gcctgacaag      60
tccgtatcag ttgcagctgg agagtcggcc attctgcact gcactgtgac ctccctgatc     120
cctgtggggc ccatccagtg gttcagagga gctggaccag cccgggaatt aatctacaat     180 caaaagaag gccacttccc ccgggtaaca actgtttcag agtccacaaa gagagaaaac     240 atggacttt ccatcagcat cagtaacatc accccagcag atgccggcac ctactactgt     300
gtgaagttcc ggaaagggag ccctgacacg gagtttaagt ctggagcagg cactgagctg     360
tctgtgcgtg ccaaaccctc tgccccgtg gtatcgggcc ctgcggcgag ggccacacct     420
cagcacacag tgagcttcac ctgcgagtcc cacggcttct cacccagaga catcaccctg     480
aaatggttca aaatgggaa tgagctctca gacttccaga ccaacgtgga ccccgtagga     540
gagagcgtgt cctacagcat ccacagcaca gccaaggtgg tgctgacccg cgaggacgtt     600
cactctcaag tcatctgcga ggtggcccac gtcaccttgc aggggaccc tcttcgtggg     660 actgccaact tgtctgagac catccgagtt ccacccacct tggaggttac tcaacagccc     720
```

```
gtgagggcag agaaccaggt gaatgtcacc tgccaggtga ggaagttcta cccccagaga    780
ctacagctga cctggttgga gaatggaaac gtgtcccgga cagaaacggc ctcaaccgtt    840
acagagaaca aggatggtac ctacaactgg atgagctggc tcctggtgaa tgtatctgcc    900 cacagggat atgtgaagct cacctgccag gtggagcatg acgggcagcc agcggtcagc     960
aaaagccatg acctgaaggt ctcagcccac ccgaaggagc agggctcaaa taccgccgct   1020
gagaacactg atctaatga acggaacgaa ttcgagccca atcttgtga caaaactcac     1080 acatgcccac cgtgcccagc acctgaactc ctgggggac cgtcagtctt cctcttcccc    1140
ccaaaaccca aggacaccct catgatctcc cggaccctg aggtcacatg cgtggtggtg     1200
gacgtgagcc acgaagaccc tgaggtcaag ttcaactggt acgtggacgg cgtggaggtg   1260
cataatgcca agacaaagcc gcgggaggag cagtacaaca gcacgtaccg tgtggtcagc    1320
gtcctcaccg tcctgcacca ggactggctg aatggcaagg agtacaagtg caaggtctcc    1380
aacaaagccc tcccagcccc catcgagaaa accatctcca aagccaaagg cagccccga    1440 gaaccacagg tgtacaccct gcccccatcc cgggatgagc tgaccaagaa ccaggtcagc    1500
ctgacctgcc tggtcaaagg cttctatccc agcgacatcg ccgtggagtg ggagagcaat    1560
gggcagccgg agaacaacta caagaccacg cctcccgtgc tggactccga cggctccttc    1620
ttcctctaca gcaagctcac cgtggacaag agcaggtggc agcaggggaa cgtcttctca    1680
tgctccgtga tgcatgaggc tctgcacaac cactacacgc agaagagcct ctccctgtct    1740
ccgggtaaat ga                                                         1752
```

```
<210> SEQ ID NO 2
<211> LENGTH: 583
<212> TYPE: PRT
<213> ORGANISM: Homo sapiens

<400> SEQUENCE: 2

Ser Cys Ala Trp Ser Gly Val Ala Gly Glu Glu Leu Gln Val Ile
1               5                   10                  15

Gln Pro Asp Lys Ser Val Ser Val Ala Ala Gly Glu Ser Ala Ile Leu
                20                  25                  30

His Cys Thr Val Thr Ser Leu Ile Pro Val Gly Pro Ile Gln Trp Phe
            35                  40                  45

Arg Gly Ala Gly Pro Ala Arg Glu Leu Ile Tyr Asn Gln Lys Glu Gly
        50                  55                  60

His Phe Pro Arg Val Thr Thr Val Ser Glu Ser Thr Lys Arg Glu Asn
65                  70                  75                  80

Met Asp Phe Ser Ile Ser Ile Ser Asn Ile Thr Pro Ala Asp Ala Gly
                85                  90                  95

Thr Tyr Tyr Cys Val Lys Phe Arg Lys Gly Ser Pro Asp Thr Glu Phe
            100                 105                 110

Lys Ser Gly Ala Gly Thr Glu Leu Ser Val Arg Ala Lys Pro Ser Ala
        115                 120                 125

Pro Val Val Ser Gly Pro Ala Ala Arg Ala Thr Pro Gln His Thr Val
    130                 135                 140

Ser Phe Thr Cys Glu Ser His Gly Phe Ser Pro Arg Asp Ile Thr Leu
145                 150                 155                 160

Lys Trp Phe Lys Asn Gly Asn Glu Leu Ser Asp Phe Gln Thr Asn Val
                165                 170                 175

Asp Pro Val Gly Glu Ser Val Ser Tyr Ser Ile His Ser Thr Ala Lys
```

```
            180                 185                 190
Val Val Leu Thr Arg Glu Asp Val His Ser Gln Val Ile Cys Glu Val
            195                 200                 205
Ala His Val Thr Leu Gln Gly Asp Pro Leu Arg Gly Thr Ala Asn Leu
            210                 215                 220
Ser Glu Thr Ile Arg Val Pro Pro Thr Leu Glu Val Thr Gln Gln Pro
225                 230                 235                 240
Val Arg Ala Glu Asn Gln Val Asn Val Thr Cys Gln Val Arg Lys Phe
                245                 250                 255
Tyr Pro Gln Arg Leu Gln Leu Thr Trp Leu Glu Asn Gly Asn Val Ser
                260                 265                 270
Arg Thr Glu Thr Ala Ser Thr Val Thr Glu Asn Lys Asp Gly Thr Tyr
            275                 280                 285
Asn Trp Met Ser Trp Leu Leu Val Asn Val Ser Ala His Arg Asp Asp
            290                 295                 300
Val Lys Leu Thr Cys Gln Val Glu His Asp Gly Gln Pro Ala Val Ser
305                 310                 315                 320
Lys Ser His Asp Leu Lys Val Ser Ala His Pro Lys Glu Gln Gly Ser
                325                 330                 335
Asn Thr Ala Ala Glu Asn Thr Gly Ser Asn Glu Arg Asn Glu Phe Glu
                340                 345                 350
Pro Lys Ser Cys Asp Lys Thr His Thr Cys Pro Pro Cys Pro Ala Pro
                355                 360                 365
Glu Leu Leu Gly Gly Pro Ser Val Phe Leu Phe Pro Pro Lys Pro Lys
            370                 375                 380
Asp Thr Leu Met Ile Ser Arg Thr Pro Glu Val Thr Cys Val Val Val
385                 390                 395                 400
Asp Val Ser His Glu Asp Pro Glu Val Lys Phe Asn Trp Tyr Val Asp
                405                 410                 415
Gly Val Glu Val His Asn Ala Lys Thr Lys Pro Arg Glu Glu Gln Tyr
                420                 425                 430
Asn Ser Thr Tyr Arg Val Val Ser Val Leu Thr Val Leu His Gln Asp
                435                 440                 445
Trp Leu Asn Gly Lys Glu Tyr Lys Cys Lys Val Ser Asn Lys Ala Leu
            450                 455                 460
Pro Ala Pro Ile Glu Lys Thr Ile Ser Lys Ala Lys Gly Gln Pro Arg
465                 470                 475                 480
Glu Pro Gln Val Tyr Thr Leu Pro Pro Ser Arg Asp Glu Leu Thr Lys
                485                 490                 495
Asn Gln Val Ser Leu Thr Cys Leu Val Lys Gly Phe Tyr Pro Ser Asp
                500                 505                 510
Ile Ala Val Glu Trp Glu Ser Asn Gly Gln Pro Glu Asn Asn Tyr Lys
                515                 520                 525
Thr Thr Pro Pro Val Leu Asp Ser Asp Gly Ser Phe Phe Leu Tyr Ser
            530                 535                 540
Lys Leu Thr Val Asp Lys Ser Arg Trp Gln Gln Gly Asn Val Phe Ser
545                 550                 555                 560
Cys Ser Val Met His Glu Ala Leu His Asn His Tyr Thr Gln Lys Ser
                565                 570                 575
Leu Ser Leu Ser Pro Gly Lys
            580

<210> SEQ ID NO 3
```

<211> LENGTH: 1131
<212> TYPE: DNA
<213> ORGANISM: Homo sapiens

<400> SEQUENCE: 3

```
tcctgcgcct ggtcaggagt ggcgggtgag gaggagctgc aggtgattca gcctgacaag      60
tccgtatcag ttgcagctgg agagtcggcc attctgcact gcactgtgac ctccctgatc     120
cctgtgggc ccatccagtg gttcagagga gctggaccag cccgggaatt aatctacaat     180
caaaaagaag gccacttccc ccgggtaaca actgtttcag agtccacaaa gagagaaaac     240
atggactttt ccatcagcat cagtaacatc accccagcag atgccggcac ctactactgt     300
gtgaagttcc ggaaagggag ccctgacacg gagtttaagt ctggagcagg cactgagctg     360
tctgtgcgtg ccaaaccctc tgccccgtg gtatcgggcc ctgcggcgag gccacacct      420
cagcacgaat tcgagcccaa atcttgtgac aaaactcaca catgcccacc gtgcccagca     480
cctgaactcc tggggggacc gtcagtcttc ctcttccccc caaaacccaa ggacaccctc     540
atgatctccc ggacccctga ggtcacatgc gtggtggtgg acgtgagcca cgaagaccct     600
gaggtcaagt tcaactggta cgtggacggc gtggaggtgc ataatgccaa gacaaagccg     660
cgggaggagc agtacaacag cacgtaccgt gtggtcagcg tcctcaccgt cctgcaccag     720
gactggctga atggcaagga gtacaagtgc aaggtctcca acaaagccct cccagccccc     780
atcgagaaaa ccatctccaa agccaaaggg cagccccgag aaccacaggt gtacaccctg     840
cccccatccc gggatgagct gaccaagaac caggtcagcc tgacctgcct ggtcaaaggc     900
ttctatccca gcgacatcgc cgtggagtgg gagagcaatg ggcagccgga gaacaactac     960
aagaccacgc ctcccgtgct ggactccgac ggctccttct tcctctacag caagctcacc    1020
gtggacaaga gcaggtggca gcaggggaac gtcttctcat gctccgtgat gcatgaggct    1080
ctgcacaacc actacacgca gaagagcctc tccctgtctc cgggtaaata g             1131
```

<210> SEQ ID NO 4
<211> LENGTH: 376
<212> TYPE: PRT
<213> ORGANISM: Homo sapiens

<400> SEQUENCE: 4

```
Ser Cys Ala Trp Ser Gly Val Ala Gly Glu Glu Leu Gln Val Ile
1               5                   10                  15

Gln Pro Asp Lys Ser Val Ser Val Ala Ala Gly Glu Ser Ala Ile Leu
            20                  25                  30

His Cys Thr Val Thr Ser Leu Ile Pro Val Gly Pro Ile Gln Trp Phe
        35                  40                  45

Arg Gly Ala Gly Pro Ala Arg Glu Leu Ile Tyr Asn Gln Lys Glu Gly
    50                  55                  60

His Phe Pro Arg Val Thr Thr Val Ser Glu Ser Thr Lys Arg Glu Asn
65                  70                  75                  80

Met Asp Phe Ser Ile Ser Ile Ser Asn Ile Thr Pro Ala Asp Ala Gly
                85                  90                  95

Thr Tyr Tyr Cys Val Lys Phe Arg Lys Gly Ser Pro Asp Thr Glu Phe
            100                 105                 110

Lys Ser Gly Ala Gly Thr Glu Leu Ser Val Arg Ala Lys Pro Ser Ala
        115                 120                 125

Pro Val Val Ser Gly Pro Ala Ala Arg Ala Thr Pro Gln His Glu Phe
    130                 135                 140
```

```
Glu Pro Lys Ser Cys Asp Lys Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
                260                 265                 270

Arg Glu Pro Gln Val Tyr Thr Leu Pro Pro Ser Arg Asp Glu Leu Thr
            275                 280                 285

Lys Asn Gln Val Ser Leu Thr Cys Leu Val Lys Gly Phe Tyr Pro Ser
290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly Lys
370                 375

<210> SEQ ID NO 5
<211> LENGTH: 1125
<212> TYPE: DNA
<213> ORGANISM: Homo sapiens

<400> SEQUENCE: 5
tcctgcgcct ggtcaggagt ggcgggtgag gaggagctgc aggtgattca gcctgacaag      60
tccgtatcag ttgcagctgg agagtcggcc attctgcact gcactgtgac ctccctgatc     120
cctgtggggc ccatccagtg gttcagagga gctggaccag cccgggaatt aatctacaat     180
caaaaagaag ccacttcccc cgggtaacaa ctgtttcag agtccacaaa gagagaaaac      240
atggactttt ccatcagcat cagtgccatc accccagcag atgccggcac ctactactgt     300
gtgaagttcc ggaaagggag ccctgacacg gagtttaagt ctggagcagg cactgagctg     360
tctgtgcgtg ccaaaccctc tgccccgtg gtatcgggcc ctgcggcgag gccacacct      420 cagcacgagc ccaaatcttg tgacaaaact cacacatgcc caccgtgccc agcacctgaa     480
ctcctggggg gaccgtcagt cttcctcttc cccccaaaac ccaaggacac cctcatgatc     540
tcccggaccc ctgaggtcac atgcgtggtg gtggacgtga gccacgaaga ccctgaggtc     600
aagttcaact ggtacgtgga cggcgtggag gtgcataatg ccaagacaaa gccgcgggag     660
gagcagtaca acagcacgta ccgtgtggtc agcgtcctca ccgtcctgca ccaggactgg     720
ctgaatggca aggagtacaa gtgcaaggtc tccaacaaag ccctcccagc ccccatcgag     780
```

```
aaaaccatct ccaaagccaa agggcagccc cgagaaccac aggtgtacac cctgccccca    840
tcccgggatg agctgaccaa gaaccaggtc agcctgacct gcctggtcaa aggcttctat    900
cccagcgaca tcgccgtgga gtgggagagc aatgggcagc cggagaacaa ctacaagacc    960
acgcctcccg tgctggactc cgacggctcc ttcttcctct acagcaagct caccgtggac   1020
aagagcaggt ggcagcaggg gaacgtcttc tcatgctccg tgatgcatga ggctctgcac   1080
aaccactaca cgcagaagag cctctcccctg tctccgggta aatag                 1125
```

<210> SEQ ID NO 6
<211> LENGTH: 374
<212> TYPE: PRT
<213> ORGANISM: Homo sapiens

<400> SEQUENCE: 6

```
Ser Cys Ala Trp Ser Gly Val Ala Gly Glu Glu Leu Gln Val Ile
 1               5                  10                  15

Gln Pro Asp Lys Ser Val Ser Val Ala Ala Gly Glu Ser Ala Ile Leu
             20                  25                  30

His Cys Thr Val Thr Ser Leu Ile Pro Val Gly Pro Ile Gln Trp Phe
         35                  40                  45

Arg Gly Ala Gly Pro Ala Arg Glu Leu Ile Tyr Asn Gln Lys Glu Gly
     50                  55                  60

His Phe Pro Arg Val Thr Thr Val Ser Glu Ser Thr Lys Arg Glu Asn
 65                  70                  75                  80

Met Asp Phe Ser Ile Ser Ile Ser Ala Ile Thr Pro Ala Asp Ala Gly
                 85                  90                  95

Thr Tyr Tyr Cys Val Lys Phe Arg Lys Gly Ser Pro Asp Thr Glu Phe
            100                 105                 110

Lys Ser Gly Ala Gly Thr Glu Leu Ser Val Arg Ala Lys Pro Ser Ala
        115                 120                 125

Pro Val Val Ser Gly Pro Ala Ala Arg Ala Thr Pro Gln His Glu Pro
    130                 135                 140

Lys Ser Cys Asp Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
    210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Thr
305                 310                 315                 320
```

Thr Pro Pro Val Leu Asp Ser Asp Gly Ser Phe Phe Leu Tyr Ser Lys
              325                 330                 335

Leu Thr Val Asp Lys Ser Arg Trp Gln Gln Gly Asn Val Phe Ser Cys
              340                 345                 350

Ser Val Met His Glu Ala Leu His Asn His Tyr Thr Gln Lys Ser Leu
              355                 360                 365

Ser Leu Ser Pro Gly Lys
              370

<210> SEQ ID NO 7
<211> LENGTH: 1125
<212> TYPE: DNA
<213> ORGANISM: Homo sapiens

<400> SEQUENCE: 7
tcctgcgcct ggtcaggagt ggcgggtgag gaggagctgc aggtgattca gcctgacaag      60
tccgtatcag ttgcagctgg agagtcggcc attctgcact gcactgtgac ctccctgatc     120
cctgtggggc ccatccagtg gttcagagga gctggaccag cccgggaatt aatctacaat     180
caaaaagaag ccacttccc cgggtaaca actgtttcag agtccacaaa gagagaaaac      240
atggactttt ccatcagcat cagtgccatc accccagcag atgccggcac ctactactgt     300
gtgaagttcc ggaaagggag ccctgacacg gagtttaagt ctggagcagg cactgagctg     360
tctgtgcgtg ccaaaccctc tgccccgtg gtatcgggcc ctgcggcgag gccacacct      420 cagcacgagc ccaaatcttg tgacaaaact cacacatgcc caccgtgccc agcacctgaa     480
ctcctggggg gaccgtcagt cttcctcttc cccccaaaac ccaaggacac cctcatgatc     540
tcccggaccc ctgaggtcac atgcgtggtg gtggccgtga gccacgaaga ccctgaggtc     600
aagttcaact ggtacgtgga cggcgtggag gtgcataatg ccaagacaaa gccgcgggag     660
gagcagtaca acagcacgta ccgtgtggtc agcgtcctca ccgtcctgca ccaggactgg     720
ctgaatggca aggagtacaa gtgcaaggtc tccaacaaag ccctcccagc ccccatcgag     780
aaaaccatct ccaaagccaa agggcagccc cgagaaccac aggtgtacac cctgcccca      840 tcccgggatg agctgaccaa gaaccaggtc agcctgacct gcctggtcaa aggcttctat     900
cccagcgaca tcgccgtgga gtgggagagc aatgggcagc cggagaacaa ctacaagacc     960
acgcctcccg tgctggactc cgacggctcc ttcttcctct acagcaagct caccgtggac    1020
aagagcaggt ggcagcaggg gaacgtcttc tcatgctccg tgatgcatga ggctctgcac    1080
aaccactaca cgcagaagag cctctccctg tctccgggta aatag                    1125

<210> SEQ ID NO 8
<211> LENGTH: 374
<212> TYPE: PRT
<213> ORGANISM: Homo sapiens

<400> SEQUENCE: 8

Ser Cys Ala Trp Ser Gly Val Ala Gly Glu Glu Leu Gln Val Ile
1               5                   10                  15

Gln Pro Asp Lys Ser Val Ser Val Ala Ala Gly Glu Ser Ala Ile Leu
              20                  25                  30

His Cys Thr Val Thr Ser Leu Ile Pro Val Gly Pro Ile Gln Trp Phe
              35                  40                  45

Arg Gly Ala Gly Pro Ala Arg Glu Leu Ile Tyr Asn Gln Lys Glu Gly
              50                  55                  60

-continued

His Phe Pro Arg Val Thr Val Ser Glu Ser Thr Lys Arg Glu Asn
65              70                  75                  80

Met Asp Phe Ser Ile Ser Ile Ser Ala Ile Thr Pro Ala Asp Ala Gly
                85                  90                  95

Thr Tyr Tyr Cys Val Lys Phe Arg Lys Gly Ser Pro Asp Thr Glu Phe
            100                 105                 110

Lys Ser Gly Ala Gly Thr Glu Leu Ser Val Arg Ala Lys Pro Ser Ala
        115                 120                 125

Pro Val Val Ser Gly Pro Ala Ala Arg Ala Thr Pro Gln His Glu Pro
    130                 135                 140

Lys Ser Cys Asp Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Ala
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
    210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly Lys
    370

<210> SEQ ID NO 9
<211> LENGTH: 40
<212> TYPE: DNA
<213> ORGANISM: Artificial sequence
<220> FEATURE:
<223> OTHER INFORMATION: Primer

<400> SEQUENCE: 9
cccaagcttg gggccaccat ggagcccgcc ggcccggccc                    40

<210> SEQ ID NO 10
<211> LENGTH: 30
<212> TYPE: DNA
<213> ORGANISM: Artificial sequence
<220> FEATURE:
<223> OTHER INFORMATION: Primer

```
<400> SEQUENCE: 10
cggaattcgt tccgttcatt agatccagtg                                    30

<210> SEQ ID NO 11
<211> LENGTH: 30
<212> TYPE: DNA
<213> ORGANISM: Artificial sequence
<220> FEATURE:
<223> OTHER INFORMATION: Primer

<400> SEQUENCE: 11
cggaattcgt gctgaggtgt ggccctcgcc                                    30

<210> SEQ ID NO 12
<211> LENGTH: 43
<212> TYPE: DNA
<213> ORGANISM: Artificial sequence
<220> FEATURE:
<223> OTHER INFORMATION: Primer

<400> SEQUENCE: 12
gaggtcacat gcgtggtggt ggccgtgagc cacgaagacc ctg                     43

<210> SEQ ID NO 13
<211> LENGTH: 40
<212> TYPE: DNA
<213> ORGANISM: Artificial sequence
<220> FEATURE:
<223> OTHER INFORMATION: Primer

<400> SEQUENCE: 13
caccaccacg catgtgacct caggggtccg ggagatcatg                         40

<210> SEQ ID NO 14
<211> LENGTH: 9
<212> TYPE: PRT
<213> ORGANISM: Homo sapiens

<400> SEQUENCE: 14

Ser Cys Ala Trp Ser Gly Val Ala Gly
1               5
```